(12) United States Patent
Lee et al.

(10) Patent No.: US 11,124,472 B2
(45) Date of Patent: Sep. 21, 2021

(54) MYOCARDIAL REGENERATION PROMOTING COMPOUNDS, PREPARATION METHOD THEREOF, AND PHARMACEUTICAL COMPOSITION

(71) Applicant: GENHEALTH PHARMA CO., LTD., Taipei (TW)

(72) Inventors: Lain-Tze Lee, Hsinchu (TW); Hui-Ping Tsai, Hsinchu (TW); Shu-Fen Huang, Taoyuan (TW); Yi-Wen Lin, Taoyuan (TW); Pi-Tsan Huang, Hsinchu (TW); Ying-Ying Wu, Taoyuan (TW); Mei-Hui Chen, Hsinchu (TW); Li-Jie Hsu, Taoyuan (TW)

(73) Assignee: GENHEALTH PHARMA CO., LTD., Taipei (TW)

( * ) Notice: Subject to any disclaimer, the term of this patent is extended or adjusted under 35 U.S.C. 154(b) by 0 days.

(21) Appl. No.: 16/378,152

(22) Filed: Apr. 8, 2019

(65) Prior Publication Data
US 2020/0317602 A1  Oct. 8, 2020

(51) Int. Cl.
| | | |
|---|---|---|
| C07C 69/24 | (2006.01) | |
| C07C 67/313 | (2006.01) | |
| C07C 69/94 | (2006.01) | |
| C07C 69/635 | (2006.01) | |
| C07C 271/22 | (2006.01) | |
| C07C 235/76 | (2006.01) | |
| C07C 235/84 | (2006.01) | |
| C07C 269/04 | (2006.01) | |
| C07C 231/02 | (2006.01) | |
| A61P 9/10 | (2006.01) | |
| C07C 235/74 | (2006.01) | |

(52) U.S. Cl.
CPC ............. *C07C 69/24* (2013.01); *A61P 9/10* (2018.01); *C07C 67/313* (2013.01); *C07C 69/635* (2013.01); *C07C 69/94* (2013.01); *C07C 231/02* (2013.01); *C07C 235/74* (2013.01); *C07C 235/76* (2013.01); *C07C 235/84* (2013.01); *C07C 269/04* (2013.01); *C07C 271/22* (2013.01); *C07C 2601/16* (2017.05)

(58) Field of Classification Search
None
See application file for complete search history.

(56) References Cited

U.S. PATENT DOCUMENTS

| 6,025,444 A | 2/2000 | Waki et al. |
|---|---|---|
| 2012/0165491 A1 | 6/2012 | Ootsuki et al. |
| 2018/0319939 A1* | 11/2018 | Chappellet ............ C08L 77/00 |

FOREIGN PATENT DOCUMENTS

| CN | 101585770 A | 11/2009 |
|---|---|---|
| CN | 109021982 A | 12/2018 |
| EP | 0596406 A1 | 5/1994 |
| EP | 1149823 A1 | 10/2001 |
| EP | 2182406 A1 | 5/2010 |
| JP | H10502338 A | 3/1998 |
| JP | 2000053766 A | 2/2000 |
| JP | 2002508323 A | 3/2002 |
| JP | 2007262050 A | 10/2007 |
| JP | 2013028642 A | 2/2013 |
| WO | 9530646 A1 | 11/1995 |
| WO | 2017197637 A1 | 11/2017 |

OTHER PUBLICATIONS

Liu et al. "Synthesis and Anticancer Activity of (E)-4-Acyloxypropenoic Acid Derivatives" Journal of Chinese Pharmaceutical Sciences, 2002, vol. 11, No. 3, pp. 73-77.*

Shi et al. "Design and Synthesis of Novel Aspirin-Caffeic Acid Ester Hybrids for Cardioprotection with Reduced Risk of Hemorrhagic Stroke" Asian Journal of Chemistry, 2015, vol. 27, No. 4, pp. 1342-1346.*

Abe et al., A Novel Class of Orally Activity Non-Peptide Bradykinin B2 Receptor Antagonists. 2. Overcoming the Species Difference between Guinea Pig and Man, Sep. 19, 1998.

Hixson et al., Hydroxycinnamoyl Glucose and Tartrate Esters and Their Role in the Formation of Ethylphenols in Wine, Dec. 5, 2016.

Montiel-Smith et al., Synthesis of New Analogs of the C-13 Docetaxel Side Chain by Asymmetric Aminohydroxylation, Jul. 1, 2002.

N. V. Suryanarayana Birudukota et al., An approach to "escape from flatland": chemo-enzymatic synthesis and biological profiling of a library of bridged bicyclic compounds, Mar. 22, 2016.

Ogawa, S., The Application of the Perkin Reaction to Phenolic Aldehydes, Jan. 28, 1927.

Shi, Z. et al., Design and Synthesis of Novel Aspirin-Caffeic Acid Ester Hybrids for Cardioprotection with Reduced Risks of Hemorrhagic Stroke, Feb. 4, 2015.

Stout, M.D. et al., Ester Derivatives of 2,6-Bis(1-pyrrolidinylmethyl)-4-benzamidophenol as Short-Acting Antiarrhythmic Agents, Aug. 1, 1989.

Ziegler T et al., Preparation of 1-O-Acyl-D-Glycopyranoses Via Chloroacetylated Glycopyranosyl Donors, Jan. 1, 1993.

Vandana Panda et al., Dietary Phenolic Acids of Macrotyloma uniflorum (Horse Gram) Protect the Rat Heart Against Isoproterenol-Induced Myocardial Infarction, Phytotherapy Research, 2016, wileyonlinelibrary.com.

* cited by examiner

*Primary Examiner* — Joseph R Kosack
(74) *Attorney, Agent, or Firm* — Rabin & Berdo, P.C.

(57) ABSTRACT

The present invention discloses a novel 3-aryl-2-propen-1-one series derivative and the synthesis processes thereof. Besides, the present invention also discloses the series derivative as a pharmaceutical composition and their use for promoting myocardial regeneration.

8 Claims, 2 Drawing Sheets

MYOCARDIAL REGENERATION PROMOTING COMPOUNDS, PREPARATION METHOD THEREOF, AND PHARMACEUTICAL COMPOSITION

BACKGROUND OF THE INVENTION

1. Field of the Invention

The present invention relates to a novel compound, a preparation method thereof and their use, and more particularly to a novel 3-aryl-2-propen-1-one series derivative, a preparation method thereof, a pharmaceutical composition comprising the same, and their use for promoting myocardial regeneration.

2. Description of the Prior Arts

Myocardial infarction, a common acute heart disease in clinical practice, is caused by abrupt interruption on blood circulation of a portion of myocardium. Consequently, myocardial cells are damaged due to lack of sufficient oxygen. In general, once myocardial infarction occurs, damaged and dead myocardial cells cannot regenerate. Only fiber scars are formed to fill and repair the region with damaged and dead myocardial cells. Although the fiber scars help to maintain heart integrity, the stiff fiber scars are not able to contract and thus further impede the reconstruction of the heart and cause dysfunction, which even causes heart diseases such as heart failure, irregular heartbeats and cardiogenic shock.

Nowadays, the treatments for myocardial infarction include interventional therapy and drug administration. For example, the interventional therapy includes balloon angioplasty, stenting and coronary artery bypass graft, and the drug administration includes thrombolytic agents, calcium channel blockers, nitrate, angiotension-converting enzyme inhibitors, β-blockers and narcotic analgesics.

Nevertheless, the developed treatments in both clinic practice and fundamental medical research field cannot improve the regeneration of the myocardial tissues but possibly cause side effects. So far, there is no effective treatment other than waiting for self-repair of damaged myocardial tissues.

Therefore, there is an urgent need to develop related technology for promoting myocardial regeneration, and to provide effective drugs for curing myocardial infarction in either clinic practice or fundamental medical research.

SUMMARY OF THE INVENTION

According to the aforementioned shortcomings, one objective of the present invention is to provide a novel compound that can improve regeneration and repair of myocardial cells, and thereby provides a non-invasive, therapeutic strategy for myocardial infarction.

To achieve the aforementioned objective, the present invention provides a novel compound represented by the following Formula (I):

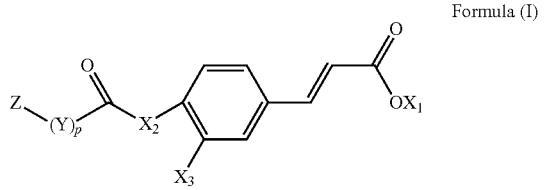

Formula (I)

wherein $X_1$ is a hydrogen atom or an unsubstituted alkyl group having 1 to 6 carbon atoms;

$X_2$ is an oxygen atom (*—O—*) or an amino group (*—NH—* or *—NX$_4$—*);

$X_3$ is a hydrogen atom (*—H), a hydroxyl group (*—OH), or *—X$_2$—(CO)—(Y)$_p$—Z group;

Y is an alkylene group having 1 to 6 carbon atoms, an alkenylene group having 2 to 12 carbon atoms, an arylenealkylene group having 7 to 18 carbon atoms, or an arylene group having 6 to 18 carbon atoms;

Z is *—COOH, *—COOCH$_3$, *—OCOCH$_3$, *—NHCOOC(CH$_3$)$_3$, *—F, *—Cl, *—Br, or *—I; and p is 0 or 1.

Preferably, in Formula (I), Z is *—COOH, *—COOCH$_3$, *—OCOCH$_3$, *—NHCOOC(CH$_3$)$_3$, or *—Cl.

In this specification, the description "an alkyl group having 1 to 6 carbon atoms" represents a linear or branched alkyl group, which indicates that the whole functional group represented by $X_1$ has 1 to 6 carbon atoms in total.

Preferably, $X_1$ may be, but is not limited to, a methyl group, an ethyl group, a propyl group, or an isopropyl group.

Preferably, in Formula (I), $X_2$ is *—NX$_4$—* and $X_4$ is *—X$_2$—(CO)—(Y)$_p$—Z group. More preferably, $X_4$ is

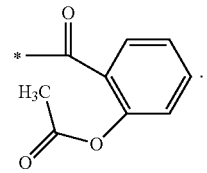

In this specification, the description "an alkylene group having 1 to 6 carbon atoms" represents a linear or branched alkylene group, which indicates that the whole functional group represented by Y has 1 to 6 carbon atoms in total. In the same way, in this specification, the description "an alkenylene group having 2 to 12 carbon atoms" represents a linear or branched alkenylene group, which indicates that the whole functional group represented by Y has 2 to 12 carbon atoms in total. In this specification, the description "an arylenealkylene group having 7 to 18 carbon atoms" represents a group containing an arylene group bonded with an alkylene group, which indicates that the whole functional group represented by Y has 7 to 18 carbon atoms in total. That is, the total carbon atoms of the arylene group and the alkylene group is 7 to 18. In this specification, the description "an arylene group having 6 to 18 carbon atoms" represents a single aromatic ring, or a polyaromatic ring formed by multiple aromatic rings bonded to or condensed with each other, which indicates that the whole functional group represented by Y has 6 to 18 carbon atoms in total.

Preferably, in Formula (I), the alkylene group having 1 to 6 carbon atoms represented by Y may be, but is not limited to, a methylene group (*—CH$_2$-*), an ethylene group (*—CH$_2$CH$_2$—*), an ethylidene group (*—CH(CH$_3$)—*), a propylene group (*—CH$_2$CH$_2$CH$_2$—*), an isopropylidene group (*—C(CH$_3$)$_2$—*), or a butylene group (*—CH$_2$CH$_2$CH$_2$CH$_2$—*). Said alkenylene group having 2 to 12 carbon atoms represented by Y may be, but is not limited to, a vinylene group (*—CH=CH—*), a propenylene group (*—CH$_2$CH=CH—* or *—CH=CHCH$_2$—*), or a butylene group (*—CH$_2$CH$_2$—CH=CH—*, *—CH$_2$CH=CHCH$_2$—* or *—CH=CHCH$_2$CH$_2$—*). Said arylenealkylene group having 7 to 18 carbon atoms represented by Y may be, but is not limited to, a cresylene group (*—CH₂C₆H₄—*), a tolylene group (*—C₆H₃(CH₃)—*), or a phenylenedimethylene group (*—CH₂C₆H₄CH₂—*). Said arylene group having 6 to 18 carbon atoms represented by Y may be, but is not limited to, a phenylene group (*—C₆H₄—*), a biphenylene group (*—C₆H₄—C₆H₄—*), or a naphthylene group (*—C₁₀H₆—*).

More specifically, in Formula (I), the phenylene group may be ortho-phenylene group, meta-phenylene group, or para-phenylene group.

Preferably, the phenylene group is ortho-phenylene group.

More specifically, in Formula (I), the cresylene group may be ortho-cresylene group, meta-cresylene group, or para-cresylene group.

Preferably, the cresylene group is meta-cresylene group.

According to the present invention, the novel compound may be, but is not limited to, any one of the following Compounds 1 to 15:

Compound 1

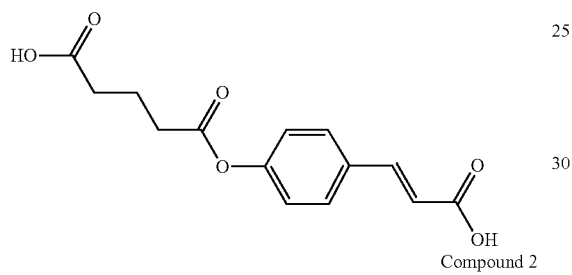

Compound 2

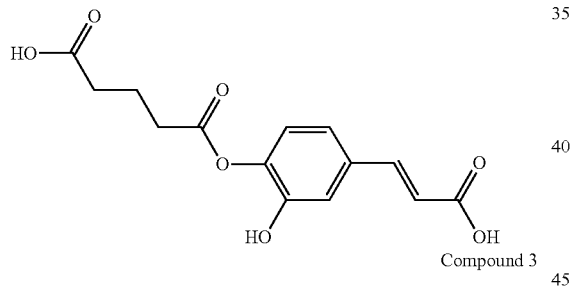

Compound 3

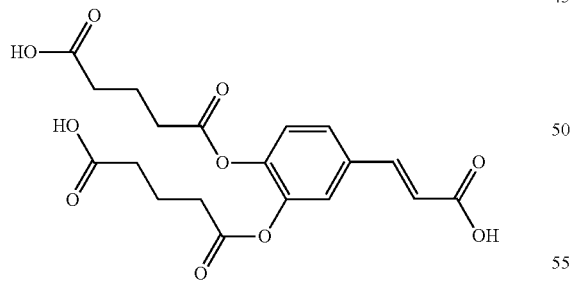

Compound 4

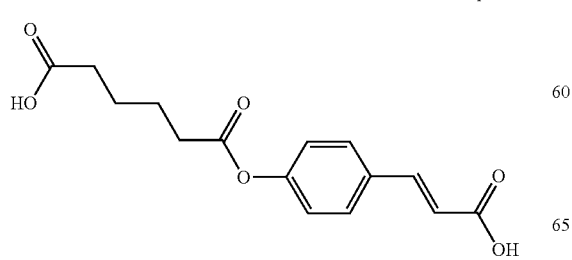

Compound 5

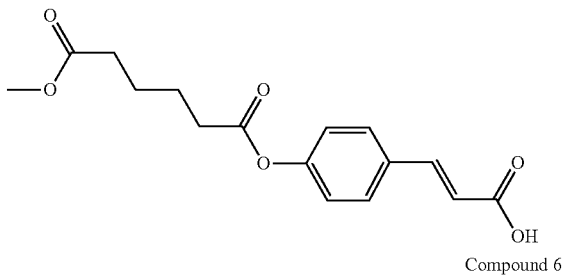

Compound 6

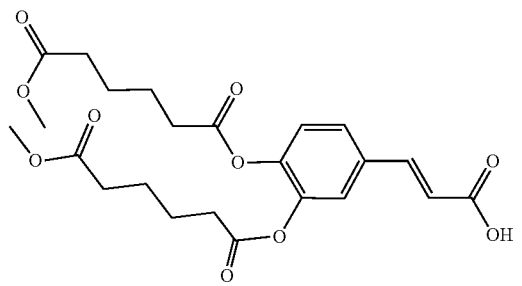

Compound 7

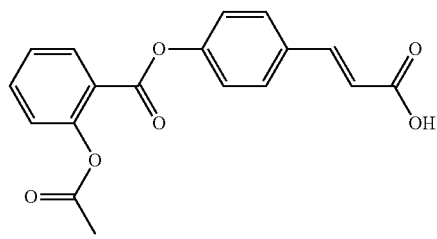

Compound 8

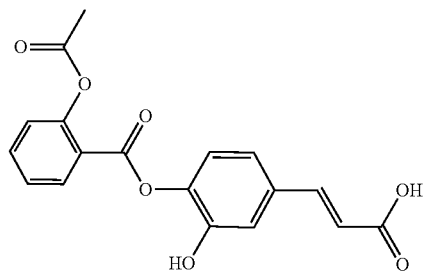

Compound 9

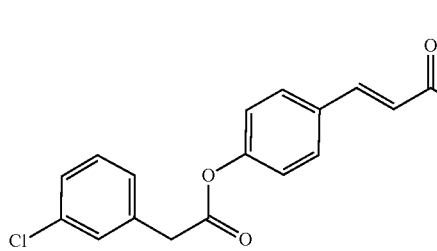

Compound 10

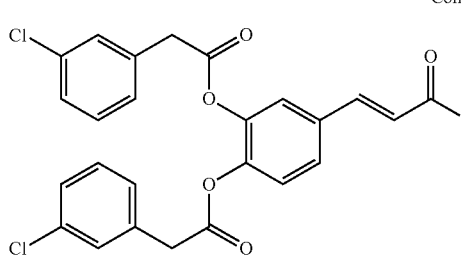

-continued

Compound 11
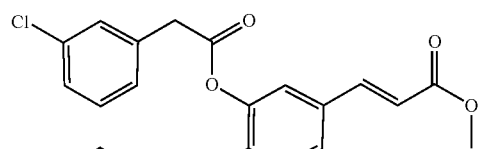

Compound 12
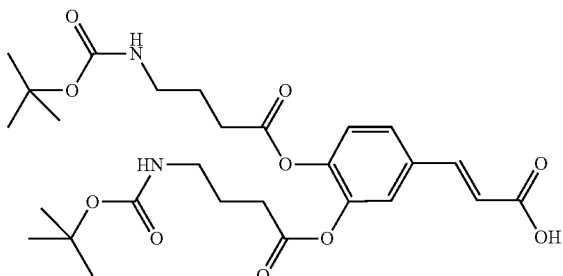

Compound 13
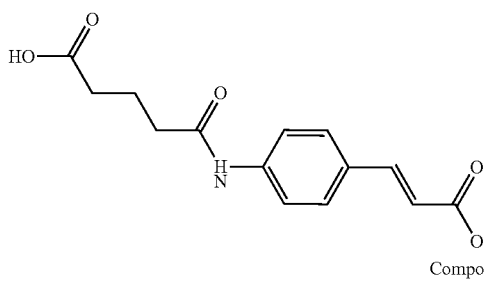

Compound 14
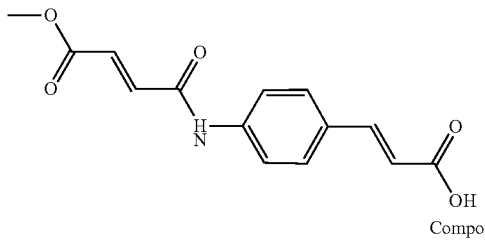

Compound 15
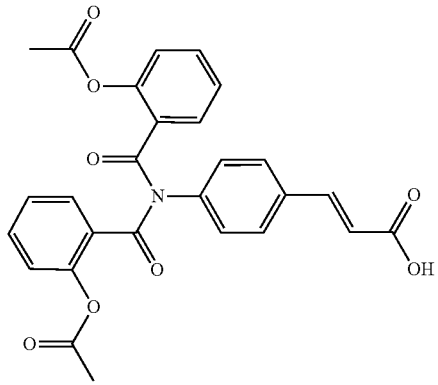

Another objective of the present invention is to provide a preparation method of the novel compound, comprising the step of reacting a reactant A with a reactant B at a temperature of 0□ to 25□. The reactant A is a coumaric acid derivative, a caffeic acid derivative, or a cinnamic acid derivative, and the reactant B is an acid compound, an anhydride compound, an acyl chloride compound, or an ester compound.

Preferably, the reaction between the reactant A and the reactant B is performed at 0□ to 25□ under alkaline conditions (within a range of pH 9 to pH 12).

Preferably, the reactant A is para-coumaric acid, caffeic acid, methyl caffeate, or 4-aminocinnamic acid.

Preferably, the reactant B is acetylsalicylic acid, 3-chlorophenylacetic acid, n-tert-butoxycarbonyl-γ-aminobutyric acid, glutaric anhydride, adipic anhydride, methyl adipoyl chloride, or fumaric acid monomethyl ester.

Another objective of the present invention is to provide a use of 3-aryl-2-propen-1-one series derivative to promote myocardial regeneration. More specifically, in this specification, the use indicates a method for promoting myocardial regeneration comprising administration of 3-aryl-2-propen-1-one series derivative.

In order to achieve the aforementioned objective, the present invention provides a method for promoting myocardial regeneration. The method comprises the administration of a therapeutically effective amount of a compound represented by the following Formula (II):

Formula (II)
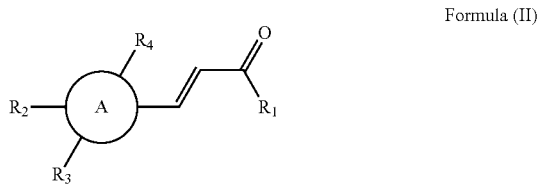

wherein $R_1$ is a hydroxyl group, an unsubstituted alkyl group having 1 to 6 carbon atoms, an unsubstituted alkoxy group having 1 to 6 carbon atoms, a substituted alkanoic acid group having 1 to 6 carbon atoms, a substituted cycloalkanoic acid group having 7 to 12 carbon atoms, a substituted or unsubstituted arylamine group having 6 to 18 carbon atoms, a substituted or unsubstituted phenolic group having 6 to 18 carbon atoms, a substituted or unsubstituted aryl group, a substituted or unsubstituted thienyl group, a substituted or unsubstituted pyrrolyl group, a substituted or unsubstituted pyridyl group, or an unsubstituted thiazolyl group;

$R_2$ is a hydrogen atom, a hydroxyl group, an unsubstituted alkyl group having 1 to 6 carbon atoms, an amino group (*—$NH_2$), an acetoxy group (*—$OCOCH_3$),

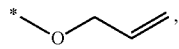

or *—$X_2(CO)$—$(Y)_p$—Z group;

$R_3$ is a hydrogen atom, a hydroxyl group, an unsubstituted alkyl group having 1 to 6 carbon atoms, an unsubstituted alkoxy group having 1 to 6 carbon atoms, or *—O—CO—$(Y)_p$—Z group; or $R_2$ and $R_3$ are joined together to form

$R_4$ is a hydrogen atom, an unsubstituted alkoxy group having 1 to 6 carbon atoms,

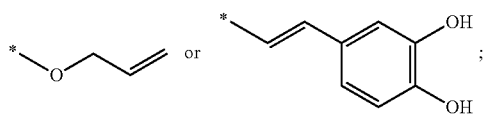

A is a benzene ring, a thiophene ring, or a pyridine ring;
$X_2$ is an oxygen atom (*—O—*) or an amino group (*—NH—* or *—$NX_4$—*);
Y is an alkylene group having 1 to 6 carbon atoms, an alkenylene group having 2 to 12 carbon atoms, an arylene-alkylene group having 7 to 18 carbon atoms, or an arylene group having 6 to 18 carbon atoms;
Z is a pyridyl group (*—$C_5H_4N$), an acetyl group (*—$COCH_3$), *—COOH, *—$COOCH_3$, *—$OCOCH_3$, *—$NHCOOC(CH_3)_3$, *—F, *—Cl, *—Br, or *—I; and
p is 0 or 1.

In brief, the 3-aryl-2-propen-1-one series derivative includes not only the aforementioned novel Compounds 1 to 15, but also other commercially accessible cinnamic acid derivative.

Preferably, in Formula (II), Z is *—$COCH_3$, *—COOH, *—$COOCH_3$, *—$OCOCH_3$, *—$NHCOOC(CH_3)_3$, or *—Cl.

Preferably, in Formula (II), $X_2$ is

or *—$NX_4$—* and $X_4$ is *—$X_2$—(CO)—$(Y)_p$—Z group.
More preferably, $X_4$ is

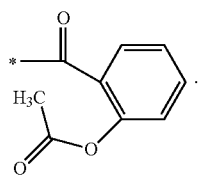

Preferably, in Formula (II), $R_3$ is *—$CH_3$,

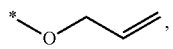

*—$NH_2$, or *—O—CO—$(Y)_p$—Z group.
Preferably, in Formula (II), when $R_2$ is *—$X_2(CO)$—$(Y)_p$—Z group, $R_1$ is a hydroxyl group.
Preferably, in Formula (II), when Y is an alkenylene group, Z is *—$COOCH_3$.
Preferably, in Formula (II), $X_2$, Y, p and Z are same as the aforementioned ones in Formula (I). In addition, in Formula (II), Z also is a pyridyl group (*—$C_5H_4N$) or an acetyl group (*—$COCH_3$).
Preferably, in Formula (II), $R_1$ is *—OH, *—$OCH_3$, *—$OCH_2C_6H_4OH$, *—$OCH(COOH)CH(OH)COOH$, *—O—$CH(COOH)CH_2(C_6H_3)(OH_2)$, *—$O(C_6H_7)(OH)_3$ (COOH), *—$NHC_6H_4OH$, *—$C_4H_3S(CH_3)$, *—$C_6H_4OH$, *—(N)—$C_4H_4N$, *—$C_5H_4N$, or *—$C_3SN(NH_2)(CH_3)$.

Preferably, the 3-aryl-2-propen-1-one series derivative, which is useful to promote regeneration and repair of damaged myocardial cells, may be, but is not limited to, any one of the aforementioned Compounds 1 to 15 and the following Compounds 16 to 46:

Compound 16

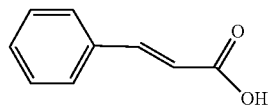

Compound 17

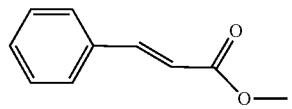

Compound 18

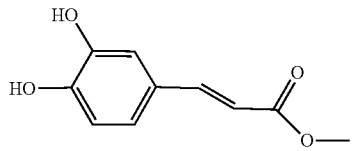

Compound 19

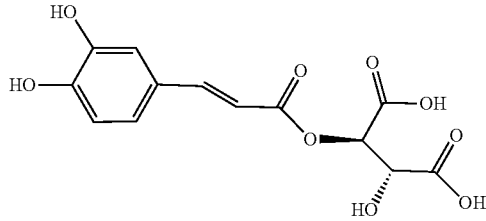

Compound 20

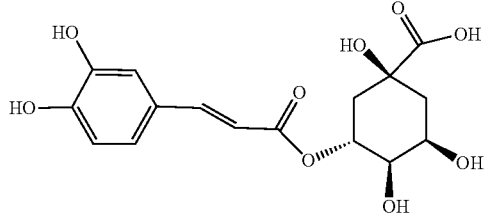

Compound 21

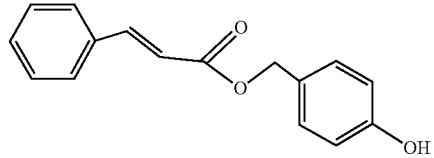

Compound 22

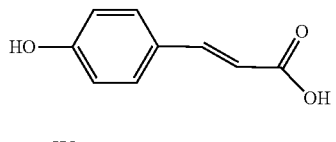

Compound 23

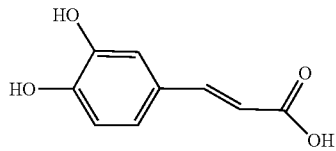

-continued

Compound 24

Compound 25

Compound 26

Compound 27

Compound 28

Compound 29

Compound 30

Compound 31

-continued

Compound 32

Compound 33

Compound 34

Compound 35

Compound 36

Compound 37

Compound 38

Compound 39

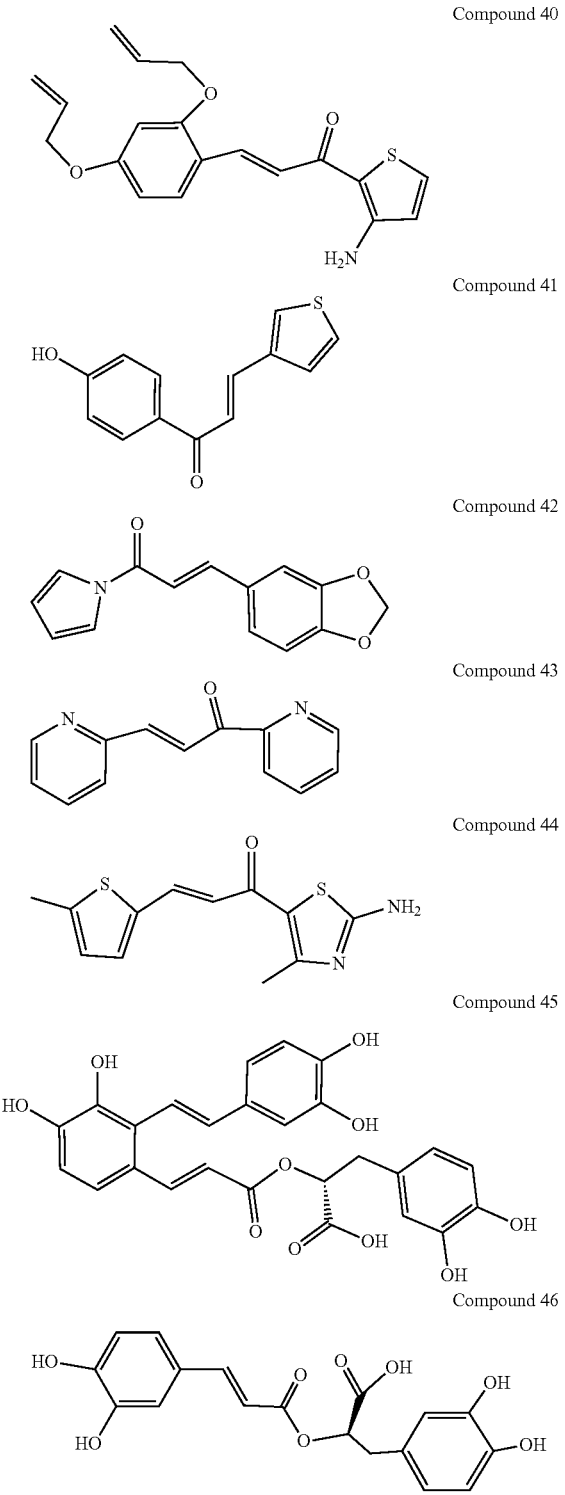

Compound 40

Compound 41

Compound 42

Compound 43

Compound 44

Compound 45

Compound 46

Besides, the present invention also provides a pharmaceutical composition for promoting myocardial regeneration. The pharmaceutical composition includes the 3-aryl-2-propen-1-one series derivative (such as Compounds 1 to 46) and a pharmaceutically acceptable carrier.

To sum up, the present invention provides a novel 3-aryl-2-propen-1-one series derivative and preparation method thereof. The novel compounds are useful to promote regeneration and repair of damaged myocardial cells. Furthermore, the present invention also provides a use of the 3-aryl-2-propen-1-one series derivative to promote myocardial regeneration.

DETAILED DESCRIPTION OF THE PREFERRED EMBODIMENTS

Figure 1:
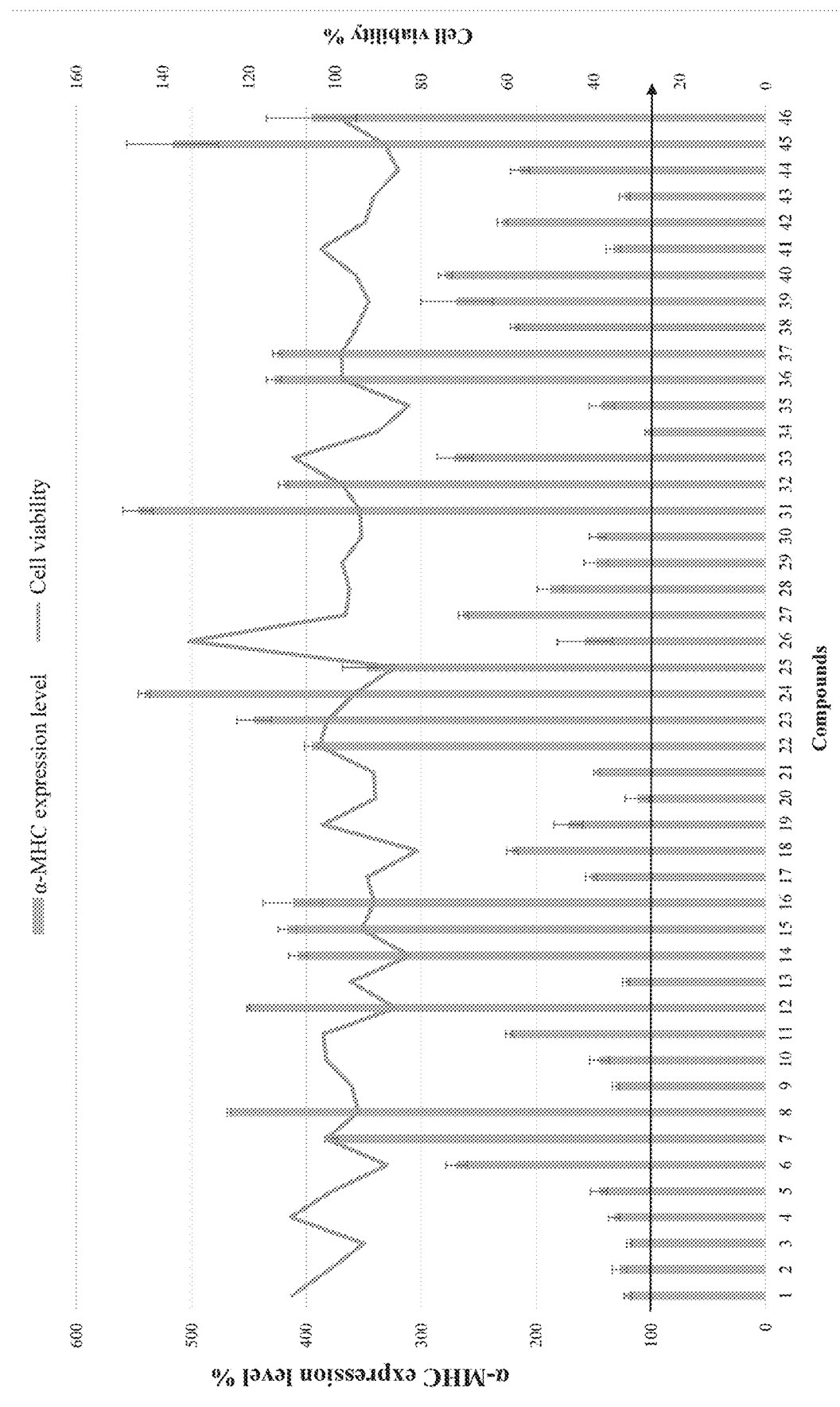
FIG. 1 shows the α-MHC expression levels of myocardial cells treated with Compounds 1 to 46; the bar graph represents the α-MHC expression level and the line graph represents the cell viability.

The following embodiments are proposed to illustrate the Compounds and the use to prepare a pharmaceutical composition for myocardial regeneration in the present invention. One person skilled in the arts can easily realize the advantages and effects of the present invention from the following examples. The descriptions proposed herein are just preferable embodiments for the purpose of illustrations only, not intended to limit the scope of the invention. Various modifications and variations could be made in order to practice or apply the present invention without departing from the spirit and scope of the invention.

PREPARATION EXAMPLE 1

Preparation of the Compounds 1 to 15

The novel compounds described in the present invention are prepared by reacting the reactant A with the reactant B at a temperature of 0☐ to 25☐ under alkaline conditions. The reactant A is a coumaric acid derivative, a caffeic acid derivative, or a cinnamic acid derivative; and the reactant B is an acid compound, an anhydride compound, an acyl chloride compound, or an ester compound.

Compound 1 para—Coumaric acid(1 g, 6.0 mmol) was dissolved in 8 ml 10% (w/w) sodium hydroxide solution, and cooled to 5° C. to 10° C. Glutaric anhydride(0.97 g, 8.4 mmol) dissolved in 5 ml tetrahydrofuran, was then slowly added into the above reaction solution. After stirring for 30 minutes, 40 ml water and 40 ml ethyl acetate were added into the reaction solution and the pH value was adjusted to 5.2. After the organic layer was separated and concentrated to dry, 50 ml water was added and the pH value was first adjusted to 9.33, and then, using1N hydrochloric acid to adjust to 5.0 for precipitation. After 1 hour stirring, the precipitate was filtered and dried to acquire 0.5335 g of a light beige powder with 100% of HPLC purity.

The structure of Compound 1 is listed in Table 1. The nuclear magnetic resonance spectroscopy of Compound 1 is as follows: $^1$H-NMR (500 MHz, DMSO-$d_6$): δ 12.255 (s, 2H), 7.723 (d, 2H), 7.577 (d, 1H), 7.166 (d, 2H), 6.494 (d, 1H), 2.618 (t, 2H), 2.330 (t, 2H), 1.841(tt, 2H). Mass spectrometry: [M+H]$^+$; $C_{14}H_{15}O_6$; 279.0859.

Compound 2

Caffeic acid(0.3 g, 1.6 mmol) was added to 6 ml acetonitrile and evenly mixed. After that, triethylamine(0.46 ml, 3.3 mmol) was added and stirred for 5 minutes. The reaction solution was cooled to 5° C. to 10° C. with an ice bath, and then glutaric anhydride(0.17 g, 1.5 mmol) dissolved in 2 ml tetrahydrofuran was slowly added. After 2 hours reaction, the reaction solution was dried out and 30 ml ethyl acetate and 30 ml 10% (w/w) ammonium chloride were added for separation. The aqueous layer was back extracted with 30 ml ethyl acetate, and the combined organic layer was dried to obtain 0.2685 g white solid. The white solid was crystallized with isopropyl acetate and acetone to acquire 0.1339 g of white powder with 100% of HPLC purity.

The structure of Compound 2 is listed in Table 1. The nuclear magnetic resonance spectroscopy of Compound 2 is as follows: $^1$H-NMR (500 MHz, $CD_3OD$): δ7.576 (d, 1H), 7.347-6.913 (m, 3H), 6.392-6.287 (dd, 1H), 2.705-2.669 (m, 2H), 2.483-2.447 (m, 2H), 2.152-1.986 (m, 2H). Mass spectrometry: $[M+H]^+$; $C_{14}H_{15}O_7$; 295.0812.

Compound 3

Caffeic acid(0.25 g, 1.4 mmol) was added to 5 ml tetrahydrofuran, and then followed by triethylamine(0.76 ml, 5.4 mmol). After stirring for several minutes, the reaction solution was concentrated to dry, and 7 ml tetrahydrofuran was added to the residue and stirred until dissolved. After cooling to 5° C. to 10° C. in an ice bath, glutaric anhydride(0.4 g, 3.4 mmol) dissolved in 3 ml tetrahydrofuran was slowly added. After 1 hour stirring, the reaction solution was dried out and 30 ml ethyl acetate and 30 ml water were added for separation. The organic layer was further washed with 30 ml brine and then dried with anhydrous sodium sulfate. The solvent was evaporated, and the residue was crystallized with isopropyl acetate and acetone to acquire 0.1629 g of white powder with 100% of HPLC purity.

The structure of Compound 3 is listed in Table 1. The nuclear magnetic resonance spectroscopy of Compound 3 is as follows: $^1$H-NMR (500 MHz, $CD_3OD$); δ7.645 (d, 1H), 7.537-7.513 (m, 2H), 7.278 (d, 1H), 6.482 (d, 1H), 2.703-2.663 (m, 4H), 2.463-2.425 (m, 4H), 2.009-1.969 (m, 4H). Mass spectrometry: $[M+NH_4]^+$; 426.1402.

Compound 4 para—Coumaric acid(1 g, 6.0 mmol ) was dissolved in 10 ml acetonitrile and then triethylamine(2.5 ml, 17.9 mmol) was added. After cooling to 0° C. to 10° C., Then a solution of glutaric anhydride(0.93 g, 7.3 mmol) dissolved in 5 ml dichloromethane was slowly added. After addition, the reaction solution was concentrated to dry to obtain a brown oil. 30 ml water was added and the aqueous layer was washed for 3 times with 30 ml of dichloromethane each and 2 times with 30 ml of ethyl acetate each. Finally, the pH value of the aqueous layer was adjusted to 4.8 to precipitate the desired compound. After filtration, 0.2542 g of white solid with 99.2% of HPLC purity was obtained.

The structure of Compound 4 is listed in Table 1. The nuclear magnetic resonance spectroscopy of Compound 4 is as follows: $^1$H-NMR (500 MHz, DMSO-$d_6$): δ 7.717 (d, 2H), 7.569 (d, 1H), 7.150 (d, 2H), 6.488 (d, 1H), 2.583 (t, 2H), 2.250 (t, 2H), 1.656-1.558 (m, 4H). Mass spectrometry: $[M+H]^+$; $C_{15}H_{17}O_6$; 293.1013.

Compound 5 para—Coumaric acid (0.333 g, 2.0 mmol) was dissolved in 10 ml anhydrous tetrahydrofuran under nitrogen, and then methyl adipoyl chloride (0.36 g, 2.0 mmol) was added with syringe. The reaction solution was cooled in an ice bath, and then slowly added ethylenediamine (0.3 g, 3.0 mmol).

After stirring at room temperature for 2 to 3 hours, the solvent was removed with rotary evaporator. Dichloromethane and water were added for liquid extraction. The organic layer was dried and the crude product was purified by column chromatography using 50% methanol as the eluent to obtain 17 mg of the product with 100% of HPLC purity.

The structure of Compound 5 is listed in Table 1. The nuclear magnetic resonance spectroscopy of Compound 5 is as follows: $^1$H-NMR (500 MHz, $CD_3OD$): δ 7.675-7.629 (m, 3H), 7.150(d, 2H), 6.463(d, 1H), 3.667(s, 3H), 2.620(t, 2H), 2.401(t, 2H), 1.751-1.736 (m, 4H). Mass spectrometry: $[M+H]^+$; $C_{16}H_{19}O_6$; 307.1181; $[M+Na]^+$; 329.1000.

Compound 6

Caffeic acid (0.369 g, 2.0 mmol) was dissolved in 10 ml anhydrous tetrahydrofuran under nitrogen, and then, methyl adipoyl chloride (0.5146 g, 3.0 mmol) was added with syringe. The solution was cooled in an ice bath, and then ethylenediamine (0.5129 g, 5.0 mmol) was slowly added. After stirring at room temperature for 2 to 3 hours, the solvent was removed with rotary evaporator. Dichloromethane and water were added for liquid extraction. After that, the organic layer was dried out. Reverse phase column chromatography with 50% to 60% aq. methanol as the eluent was used to obtain 13.8 mg of the product with 100% of HPLC purity.

The structure of Compound 6 is listed in Table 1. The nuclear magnetic resonance spectroscopy of Compound 6 is as follows: $^1$H-NMR (500 MHz, $CD_3OD$): δ7.635(d, 1H), 7.523(dd, 1H), 7.498(d, 1H), 7.264(d, 1H); 6.481(d, 1H), 3.670(s, 6H), 2.638-2.599 (m, 4H), 2.418-2.384 (m, 4H), 1.747-1.723 (m, 8H). Mass spectrometry: $[M+NH_4]^+$; 482.2059.

Compound 7 para—Coumaric acid(1 g, 6.0 mmol) was dissolved in 10 ml 10% (w/w) sodium hydroxide solution. After cooling to 5° C. to 10° C., Subsequently, a solution of acetylsalicylic anhydride(2.45 g, 7.2 mmol) dissolved in 3 ml tetrahydrofuran was then slowly added. After stirring for 30 minutes, the reaction solution was evaporated, and 30 ml water and 40 ml ethyl acetate were added. The organic layer was washed again with 20 ml water in which the pH value was adjusted to 4 to 5. The organic layer was further washed for 3 times with 5% ammonium chloride solution, and then 40 ml water while the pH value was adjusted to 6.0 by sodium bicarbonate. After separation, the organic layer was dried with anhydrous sodiumsulfate. After that, the solution was concentrated to dry to acquire 1.9 g of white solid. 30 ml dichloromethane was added to the obtained solid and washed for 2 times with water, while the pH value was adjusted to 7.37. The organic layer was then dried with anhydrous sodium sulfate and concentrated to dry to obtain 49.6 mg of white solid with 89.9% of HPLC purity.

The structure of Compound 7 is listed in Table 1. The nuclear magnetic resonance spectroscopy of Compound 7 is as follows: $^1$H-NMR (500 MHz, $CD_3OD$): δ8.200 (dd, 1H), 7.741-7.682 (m, 4H), 7.459 (t, 1H), 7.259-7.241 (m, 3H), 6.500 (d, 1H), 2.264 (s, 3H). Mass spectrometry: $[M+H]^+$; $C_{18}H_{15}O_6$; 327.0860; $[M+Na]^+$; 349.0677.

Compound 8

Acetylsalicylic acid(1.8 g, 10.0 mmol), 20 ml toluene and 3 drops of dimethylformamide were added into a 250 ml single-neck flask. After stirring at 40° C. for 3 minutes, thionyl chloride(1.8 ml, 24.8 mmol) was added into the reaction solution and then heated at 60° C. for 2 hours. After cooled to 25° C., excess thionyl chloride and all solvent were removed with rotary evaporator.

20 ml toluene was added into the reaction solution and the solvent was removed again to obtain a light yellow liquid. Afterwards, caffeic acid(1.81 g, 10.0 mmol), 20 ml tetrahydrofuran and triethylamine(1.5 ml, 10.0 mmol) were added into the liquid and stirred at room temperature for 3 hours. Then 20 ml saturated ammonium chloride solution was added. After separation, the organic layer was evaporated to obtain 4.82 g of an off-white solid. The solid was dissolved in 40 ml ethyl acetate and washed with 40 ml water. The organic layer was dried, filtered and evaporated to yield 3.74 g of orange liquid. Column chromatography (silica gel: 63.4 g; the diameter of the column: 4.5 cm; the length of the column: 13.5 cm; and the eluent being dichloromethane: methanol=1:0 to 50:1) was applied to collect the desired product, which was purified again with column chromatography to yield 56 mg of desired compound with 94.6% of HPLC purity.

The structure of Compound 8 is listed in Table 1. The nuclear magnetic resonance spectroscopy of Compound 8 is as follows: $^1$H-NMR (500 MHz, CD$_3$OD): δ8.242-8.207 (m, 1H), 7.708(t, 1H), 7.602 (d, 1H), 7.451 (t, 1H), 7.407-6.968 (m, 4H), 6.425-6.312(dd, 1H), 2.266(s, 3H). Mass spectrometry: [M+H]$^+$; C$_{18}$H$_{15}$O$_7$; 343.0822; [M+NH$_4$]$^+$; 360.1091.

Compound 9

A mixture of para-coumaric acid(0.304 g, 2.0 mmol), triethylamine(2.9 ml, 28.0 mmol) and 4.0 ml acetonitrile were added to the crude pre-prepared 3-chlorophenylacetyl chloride(0.8 g, 1.4 mmol), which was cooled in an ice bath. After the addition, the ice bath was removed and the solution was stirred at room temperature for 1 hour. Water and 1,2-dichloroethane were added into the reaction solution for extraction, while the pH was adjusted around 6.0. After stirring for 0.5 hour, layers separated and the solvent of the organic layer was evaporated to leave a residue(2.8 g), which was purified by the silica gel column chromatography (the eluent being ethyl acetate:dichloromethane=1:1.5) to yield 26 mg of white solid with 87.8% of HPLC purity.

The structure of Compound 9 is listed in Table 1. The nuclear magnetic resonance spectroscopy of Compound 9 is as follows: $^1$H-NMR (500 MHz, CD$_3$OD): δ 7.661(d, 1H), 7.635 (d, 2H), 7.423 (s, 1H), 7.342(d, 1H), 7.324-7.312 (m, 2H), 7.146 (d, 2H), 6.457 (d, 1H), 3.939 (s, 2H). Mass spectrometry: [M+H]$^+$; C$_{17}$H$_{14}$ClO$_4$; 317.0580.

Compound 10

3—Chlorophenylacetic acid(1.71 g, 10.0 mmol), 20 ml toluene and 2 drops of dimethylformamide were added into a 250 ml single-neck flask. After stirring at 24° C. for 5 minutes, thionyl chloride(1.5 ml, 20.7 mmol) was added, and heated at 65° C. for 1 hour. After cooled to 25° C., excess thionyl chloride and solvent were removed with rotary evaporator. Then 25 ml tetrahydrofuran was added into the reaction solution and the solvent was removed again to obtain 2.18 g of a light yellow liquid. Subsequently, caffeic acid(1.81 g, 10.0 mmol), 20 ml tetrahydrofuran and triethylamine(1.4 ml, 10 mmol) were added to the liquid and the reaction solution was stirred at room temperature for 4 hours. Then 20 ml saturated ammonium chloride solution was added to separate the organic layer. The solvent of the organic layer was removed with rotary evaporator to obtain 5.13 g of a off-white solid. The solid was purified by column chromatography (silica gel: 67.4 g; the diameter of the column: 4 cm; the length of the column: 14 cm; and the eluent being ethyl acetate:heptane=1:3 to 1:1) to collect the desired product with 97.6% of HPLC purity.

The structure of Compound 10 is listed in the Table 1. The nuclear magnetic resonance spectroscopy of Compound 10 is as follows: $^1$H-NMR (500 MHz, CD$_3$OD): δ 7.613(d, 1H), 7.511-7.478 (m, 2H), 7.356-7.281 (m, 6H), 7.250-7.214 (m, 3H), 6.455(d, 1H), 3.726(s, 2H), 3.696(s, 2H).Mass spectrometry: [M+H]$^+$; C$_{25}$H$_{19}$Cl$_2$O$_6$; 485.0569.

Compound 11

3-Chlorophenylacetic acid(0.43 g, 2.5 mmol), 10 ml toluene and 2 drops of dimethylformamide were added into a 100 ml single-neck flask. After stirring at 24° C. for 10 minutes, thionyl chloride(0.5 ml, 6.9 mmol) was added and heated at 65° C. for 1 hour. After the reaction solution was cooled to 25° C., excess thionyl chloride and solvent were removed with rotary evaporator. Then 10 ml toluene was added into the reaction solution, and the solvent was removed again to obtain a light yellow liquid. Subsequently, methyl caffeate(0.49 g, 2.5 mmol), 10 ml tetrahydrofuran and triethylamine(0.4 ml, 2.9 mmol) were added into the liquid and the reaction solution was stirred at room temperature for 3 hours. Then 20 ml saturated ammonium chloride solution was added to separate the organic layer. Afterwards, the organic layer was washed with 20 ml saturated sodium bicarbonate solution and 20 ml water. The organic layer was dried, filtered and evaporated to obtain an orange liquid. Column chromatography (silica gel: 51.6 g; the diameter of the column: 4.5 cm; the length of the column: 10 cm; and the eluent being ethyl acetate:heptane=1:5) was applied to collect 27.3 mg of product with 98.6% of HPLC purity.

The structure of Compound 11 is listed in Table 1. The nuclear magnetic resonance spectroscopy of Compound 11 is as follows: $^1$H-NMR (500 MHz, CD$_3$OD): δ 7.618(d, 1H), 7.503-7.476 (m, 2H), 7.344-7.266 (m, 6H), 7.242-7.205 (m, 3H), 6.490(d, 1H), 3.767(s, 3H), 3.713(s, 2H), 3.686(s, 2H). Mass spectrometry: [M+H]$^+$; C$_{26}$H$_{21}$Cl$_2$O$_6$; 499.0719.

Compound 12 n-tert-Butoxycarbonyl-α-aminobutyric acid(1.59 g, 7.8 mmol) was added into a 250 ml single-neck flask under nitrogen. Then 8 ml tetrahydrofuran and triethylamine(2.2 ml, 15.8 mmol) were added and the reaction solution was stirred at −20° C. for 5 minutes. After that, a mixture of trimethylacetyl chloride(0.96 ml, 7.8 mmol) and 5 ml tetrahydrofuran was added into the reaction solution in 10 minutes, and stirred at 0° C. for 2 hours.

Then a mixture of caffeic acid(0.7 g, 3.9 mmol) and 8 ml tetrahydrofuran was added into the reaction solution in 2 minutes, and stirred at room temperature for 45 hours. 30 ml saturated ammonium chloride solution was then added. The organic layer was separated and evaporated. 30 ml ethyl acetate was added to the residue and washed with 30 ml water. Afterwards, the solvent of the organic layer was removed to obtain 2.13 g of a white solid. After the column chromatography (silica gel: 65 g; the diameter of the column: 4 cm; the length of the column: 15 cm; and the eluent being dichloromethane: methanol=50:1 to 20:1) purification, 17.8 mg of product with 97.4% of HPLC purity was obtained.

The structure of Compound 12 is listed in Table 1. The nuclear magnetic resonance spectroscopy of Compound 12 is as follows: $^1$H-NMR (500 MHz, CD$_3$OD): δ 7.644 (d, 1H), 7.535-7.507(m, 2H), 7.293 (d, 1H), 6.845(d, 1H), 3.173-3.134(m, 4H), 2.637-2.596(m, 4H), 1.885-1.846(m, 4H), 1.440(s, 18H). Mass spectrometry: [M+H]$^+$; C$_{27}$H$_{39}$N$_2$O$_{10}$; 551.2591; [M+Na]$^+$;573.2414.

Compound 13

At room temperature, 4-aminocinnamic acid(0.201 g, 1.0 mmol) and 2 ml tetrahydrofuran were mixed, and then glutaric anhydride(0.169 g, 2.0 mmol) was added and stirred for 1.5 hours. After that, the precipitate was filtered and washed with water to obtain 0.336 g of white solid with 98.2% of HPLC purity.

The structure of Compound 13 is listed in Table 1. The nuclear magnetic resonance spectroscopy of Compound 13 is as follows: $^1$H-NMR (500 MHz, CD$_3$OD): δ 7.643-7.611 (m, 3H), 7.551(d, 2H), 6.401(d, 1H), 2.454(t, 2H), 2.393(t, 2H), 1.978(tt, 2H). Mass spectrometry: [M+H]$^+$; C$_{14}$H$_{16}$NO$_5$; 278.1067.

Compound 14

Fumaric acid monomethyl ester(0.72 g, 5.5 mmol), 10 ml toluene and 2 drops of dimethylformamide were added into a 100 ml single-neck flask. After stirring at 17° C. for 3 minutes, 0.9 ml thionyl chloride(11.0 mmol) was added and heated at 60° C. for 3 hours. After the reaction solution was cooled to 30° C., excess thionyl chloride and all solvent were removed with rotary evaporator. Then 4-aminocinnamic acid(0.82 g, 5.0 mmol), 10 ml tetrahydrofuran and triethylamine(1.4 ml, 10.0 mmol) were added into the residue and stirred at 0° C. for 30 minutes, and then 19 hours at room temperature. After that, 20 ml saturated ammonium chloride solution and 5 ml water were added into the reaction solution to separate the organic layer. The aqueous layer was back extracted for 2 times with 20 ml of dichloromethane. The combined organic layer was dried, filtered and evaporated to yield a yellow solid, which was purified by column chromatography (silica gel: 52.9 g; the diameter of the column: 4 cm; the length of the column: 11 cm; and the eluent being ethyl acetate:heptane=1:3 to 1:0) to obtain 22.5 mg of desired product with 94.0% of HPLC purity.

The structure of Compound 14 is listed in Table 1. The nuclear magnetic resonance spectroscopy of Compound 14 is as follows: $^1$H-NMR (500 MHz, DMSO-d$_6$): δ 12.283(br s,1H), 10.709(s,1H), 7.707 (d, 2H), 7.663(d, 2H), 7.523(d, 1H), 7.211(d, 1H), 6.726(d, 1H), 6.430(d, 1H), 3.746(s,3H). Mass spectrometry: [M+H]$^+$; $C_{14}H_{14}NO_5$; 276.0866.

Compound 15

Acetylsalicylic acid(1.0 g, 5.5 mmol), 20 ml toluene and 3 drops of dimethylformamide were added into a 100 ml single-neck flask. After stirring at 20° C. for 3 minutes, thionyl chloride(0.9 ml, 11.0 mmol) was added and heated at 60° C. for 1.5 hours. After cooled to 35° C., excess thionyl chloride and all solvent were removed with rotary evaporator. Afterwards, 10 ml tetrahydrofuran was added to the residue and evaporated again to obtain 1 g of light yellow liquid. Then 4-aminocinnamic acid(0.81 g, 5.0 mmol), 10 ml tetrahydrofuran and 1.4 ml triethylamine(10.0 mmol) were added and stirred first at 0° C. for 1 hour, and then at room temperature for 22 hours. After that, 25 ml saturated ammonium chloride solution and 5 ml water were added into the reaction solution to separate the organic layer. The solvent was removed with rotary evaporator to acquire 0.91 g of yellow solid. After the column chromatography (silica gel: 64.7 g; the diameter of the column: 4 cm; the length of the column: 12.5 cm; and the eluent being ethyl acetate: heptane=1:5 to 1:1) purification, 10.7 mg of product with 92.7% of HPLC was obtained.

The structure of Compound 15 is listed in Table 1. The nuclear magnetic resonance spectroscopy of Compound 15 is as follows: $^1$H-NMR (500 MHz, DMSO-d$_6$):δ 10.523(s, 1H), 7.948(dd,1H), 7.765 (td, 1H), 7.700(d, 2H), 7.666-7.627(m, 3H), 7.564(td, 1H), 7.508(d, 1H), 7.378(t, 1H), 7.321(t,1H), 7.236(d,2H), 6.369(d,1H), 2.230(s, 3H), 2.154 (s, 3H). Mass spectrometry: [M+H]$^+$; $C_{27}H_{22}NO_8$; 488.1348; [M+Na]$^+$; 510.1171.

TABLE 1 the structures of Compounds 1 to 15

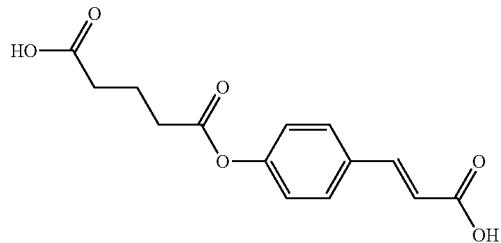

Compound 1

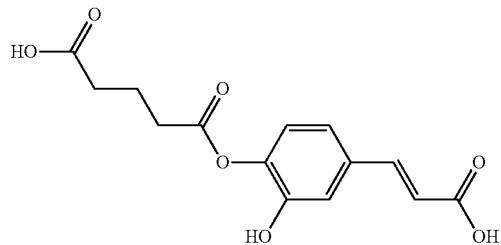

Compound 2

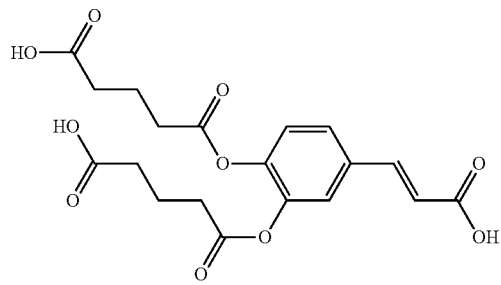 [SMILES: O=C(O)/C=C/c1ccc(OC(=O)CCCC(=O)O)c(OC(=O)CCCC(=O)O)c1]

Compound 3

TABLE 1-continued
the structures of Compounds 1 to 15
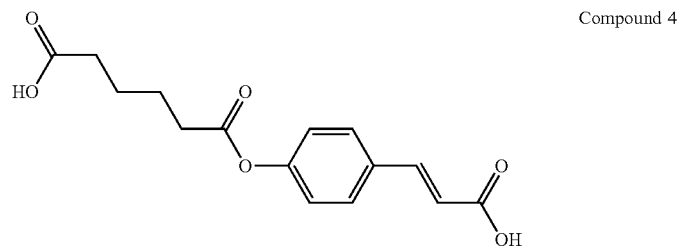
Compound 4
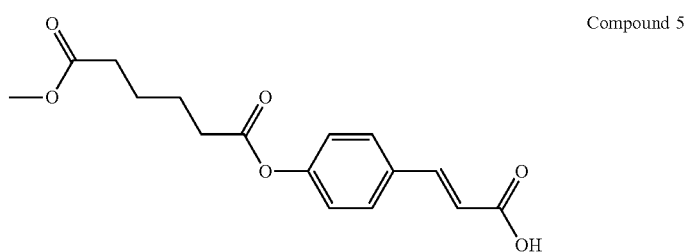
Compound 5
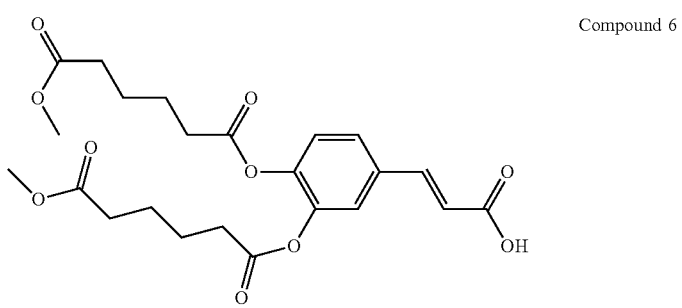
Compound 6
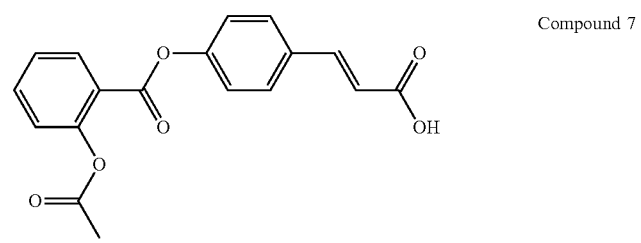
Compound 7
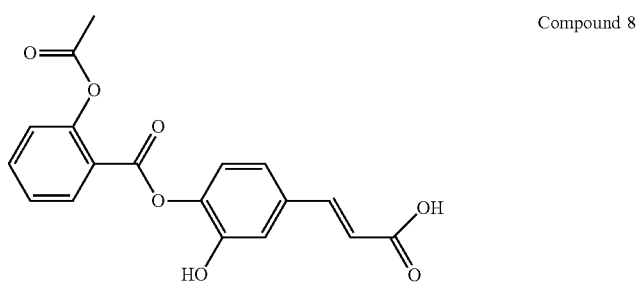
Compound 8
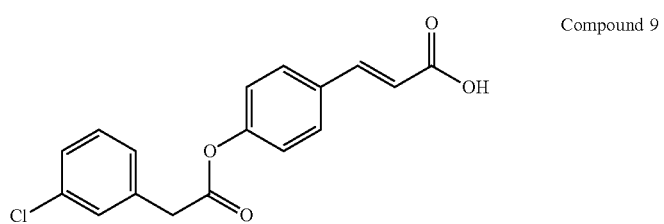
Compound 9

TABLE 1-continued
the structures of Compounds 1 to 15
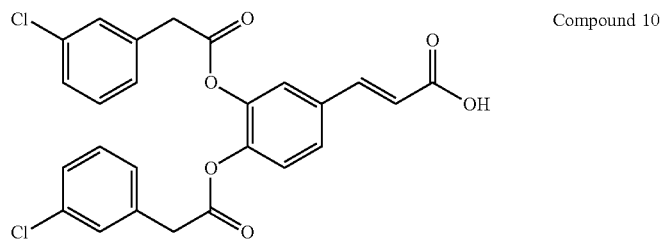
Compound 10
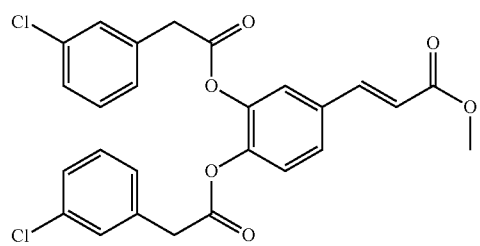 [SMILES: COC(=O)/C=C/c1ccc(OC(=O)Cc2cccc(Cl)c2)c(OC(=O)Cc2cccc(Cl)c2)c1]
Compound 11
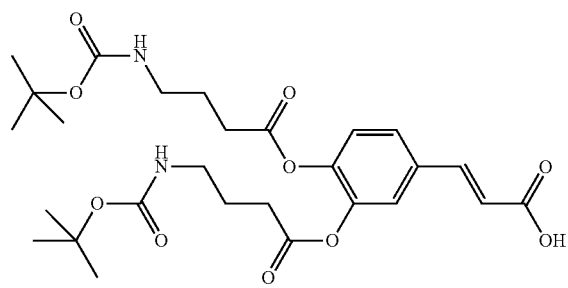 [SMILES: CC(C)(C)OC(=O)NCCCC(=O)Oc1ccc(/C=C/C(=O)O)cc1OC(=O)CCCNC(=O)OC(C)(C)C]
Compound 12
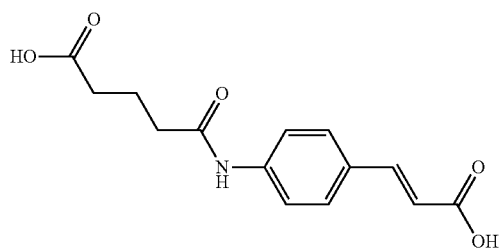
Compound 13
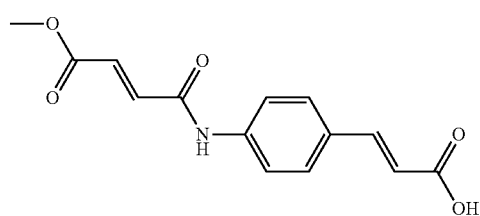
Compound 14

TABLE 1-continued the structures of Compounds 1 to 15

Compound 15

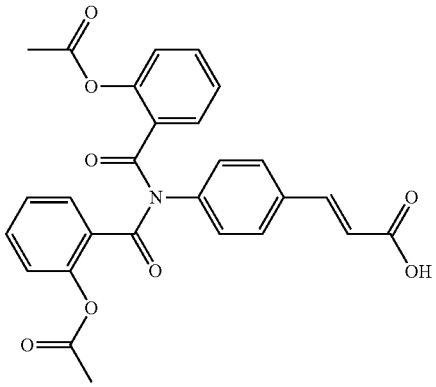 [SMILES: CC(=O)Oc1ccccc1C(=O)N(C(=O)c1ccccc1OC(C)=O)c1ccc(/C=C/C(=O)O)cc1]

PREPARATION EXAMPLE 2

The Use of the Compounds 1 to 46 for Improving Myocardial Regeneration

The compound represented by the following Formula (II) is able to promote myocardial regeneration and the repair of the damaged myocardial cells:

Formula (II)

In Formula (II), $R_1$ is a hydroxyl group, an unsubstituted alkyl group having 1 to 6 carbon atoms, an unsubstituted alkoxy group having 1 to 6 carbon atoms, a substituted alkanoic acid group having 1 to 6 carbon atoms, a substituted cycloalkanoic acid group having 7 to 12 carbon atoms, a substituted or unsubstituted arylamine group having 6 to 18 carbon atoms, a substituted or unsubstituted phenolic group having 6 to 18 carbon atoms, a substituted or unsubstituted aryl group, a substituted or unsubstituted thienyl group, a substituted or unsubstituted pyrrolyl group, a substituted or unsubstituted pyridyl group, or an unsubstituted thiazolyl group; $R_2$ is a hydrogen atom, a hydroxyl group, an unsubstituted alkyl group having 1 to 6 carbon atoms, an amino group (*—$NH_2$), an acetoxy group (*—$OCOCH_3$),

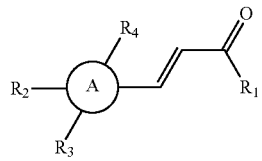

or *—$X_2(CO)$—$(Y)_p$—Z group;

$R_3$ is a hydrogen atom, a hydroxyl group, an unsubstituted alkyl group having 1 to 6 carbon atoms, an unsubstituted alkoxy group having 1 to 6 carbon atoms, or *—O—CO—$(Y)_p$—Z group; or $R_2$ and $R_3$ are joined together to form

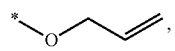

$R_4$ is a hydrogen atom, an unsubstituted alkoxy group having 1 to 6 carbon atoms,

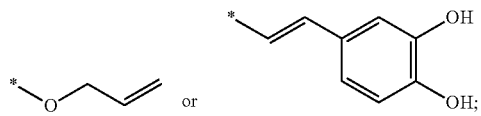

A is a benzene ring, a thiophene ring, or a pyridine ring;

$X_2$ is an oxygen atom (*—O—*) or an amino group (*—NH—* or *—$NX_4$—*);

Y is an alkylene group having 1 to 6 carbon atoms, an alkenylene group having 2 to 12 carbon atoms, an arylenealkylene group having 7 to 18 carbon atoms, or an arylene group having 6 to 18 carbon atoms;

Z is *—$C_5H_4N$, *—$COCH_3$, *—COOH, *—$COOCH_3$, *—$OCOCH_3$, *—$NHCOOC(CH_3)_3$, *—F, *—Cl, *—Br, or *—I; and is 0 or 1.

In addition to the aforementioned Compounds 1 to 15, the compounds represented by Formula (II) also include Compounds 16 to 46. The structures of Compounds 16 to 46 are listed in Table 2.

TABLE 2
the structures of Compounds 16 to 46
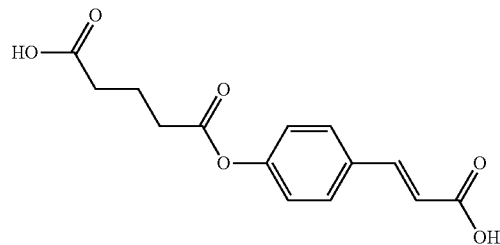
Compound 1
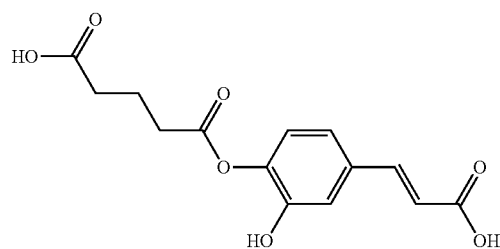 [SMILES: O=C(O)/C=C/c1ccc(OC(=O)CCCC(=O)O)c(O)c1]
Compound 2
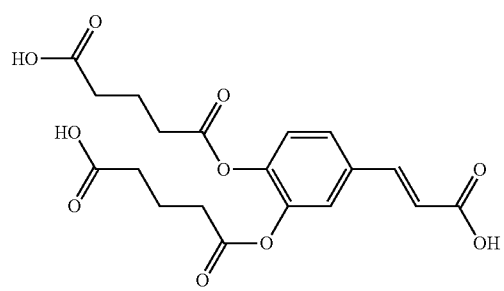 [SMILES: O=C(O)/C=C/c1ccc(OC(=O)CCCC(=O)O)c(OC(=O)CCCC(=O)O)c1]
Compound 3
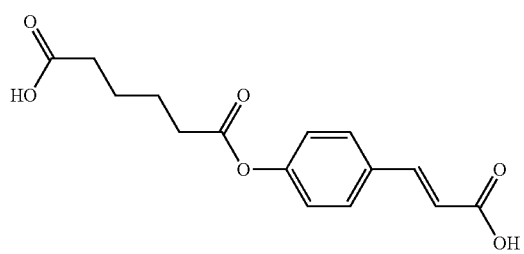 [SMILES: O=C(O)/C=C/c1ccc(OC(=O)CCCCC(=O)O)cc1]
Compound 4
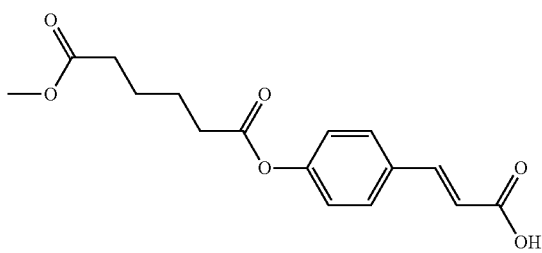 [SMILES: COC(=O)CCCCC(=O)Oc1ccc(/C=C/C(=O)O)cc1]
Compound 5
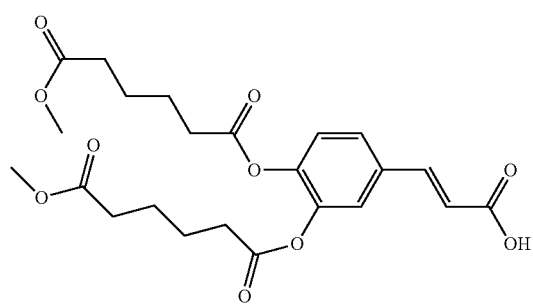 [SMILES: COC(=O)CCCCC(=O)Oc1ccc(/C=C/C(=O)O)cc1OC(=O)CCCCC(=O)OC]
Compound 6

TABLE 2-continued
the structures of Compounds 16 to 46
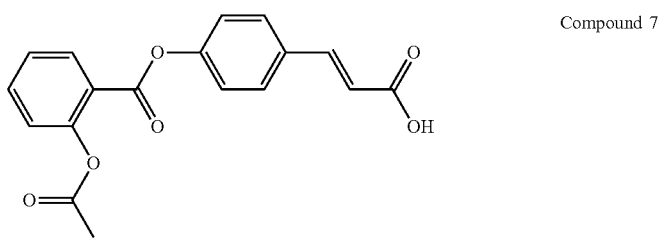
Compound 7
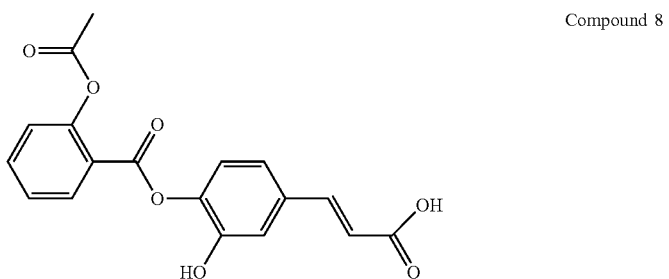
Compound 8
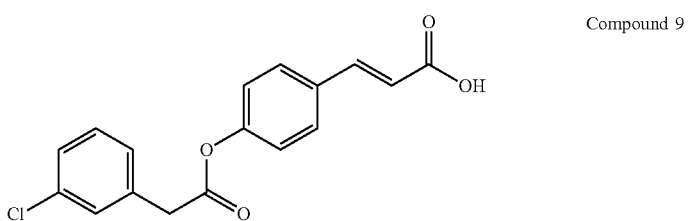
Compound 9
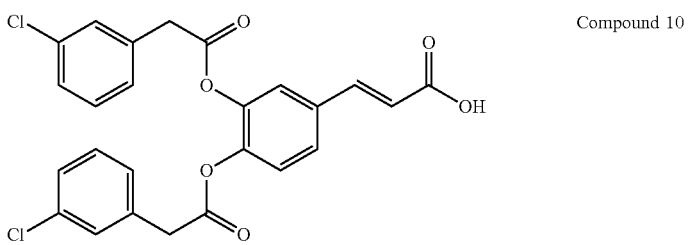
Compound 10
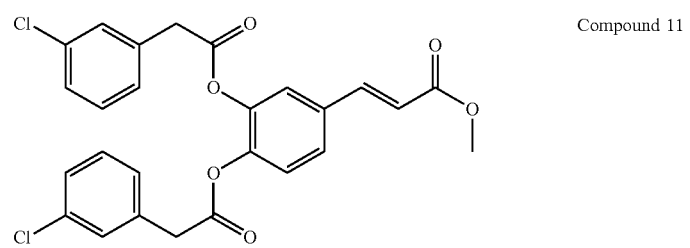
Compound 11
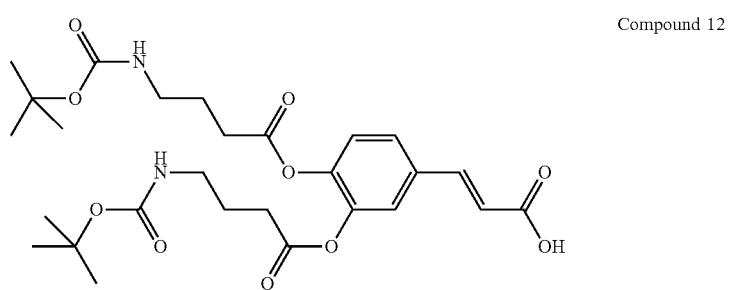
Compound 12

TABLE 2-continued
the structures of Compounds 16 to 46
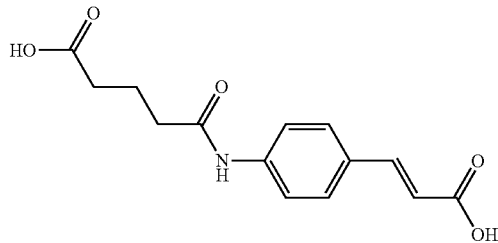
Compound 13
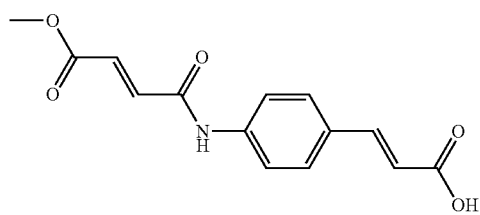 [SMILES: COC(=O)/C=C/C(=O)Nc1ccc(/C=C/C(=O)O)cc1]
Compound 14
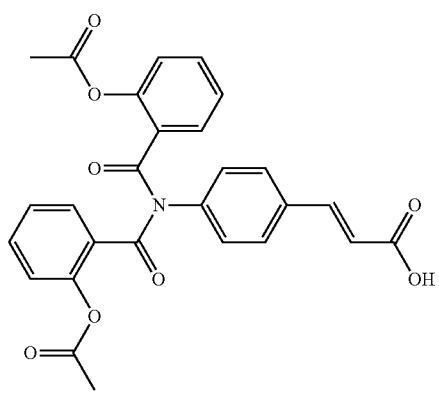 [SMILES: CC(=O)Oc1ccccc1C(=O)N(C(=O)c1ccccc1OC(C)=O)c1ccc(/C=C/C(=O)O)cc1]
Compound 15
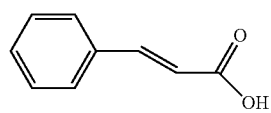 [SMILES: O=C(O)/C=C/c1ccccc1]
Compound 16
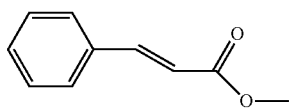
Compound 17
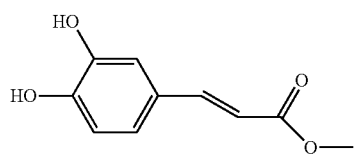
Compound 18
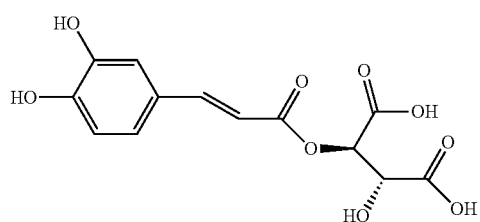 [SMILES: O=C(/C=C/c1ccc(O)c(O)c1)O[C@@H](C(=O)O)[C@@H](O)C(=O)O]
Compound 19

TABLE 2-continued
the structures of Compounds 16 to 46
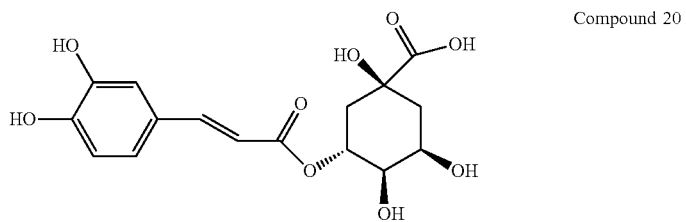 Compound 20
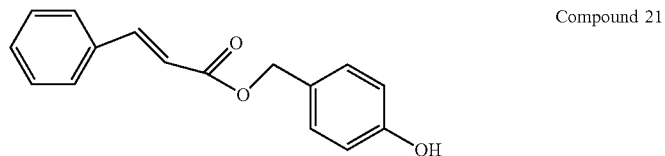 Compound 21
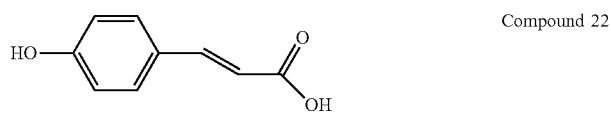 Compound 22
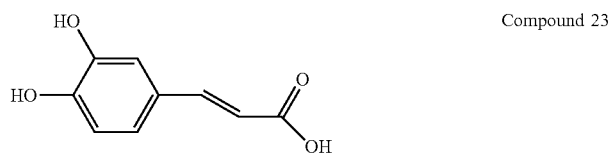 Compound 23
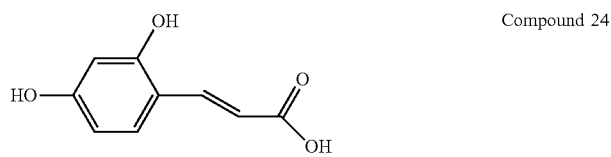 Compound 24
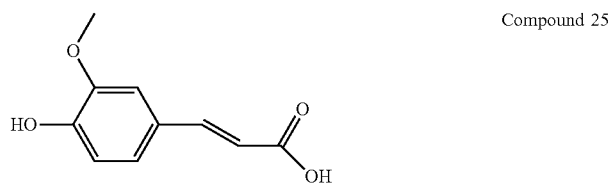 Compound 25
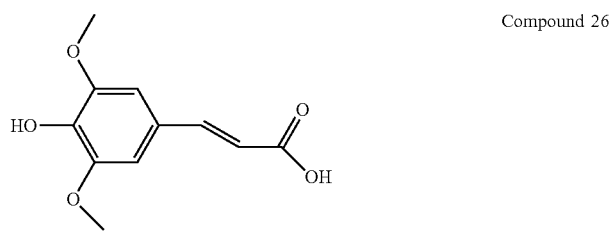 Compound 26
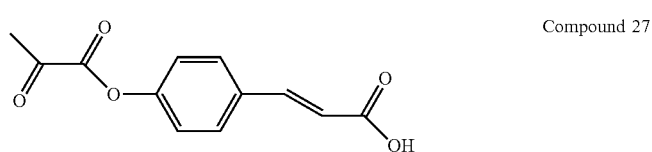 Compound 27
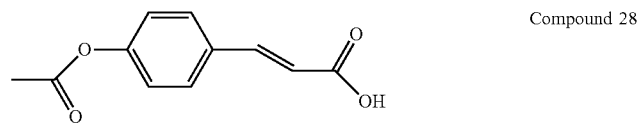 Compound 28

TABLE 2-continued
the structures of Compounds 16 to 46
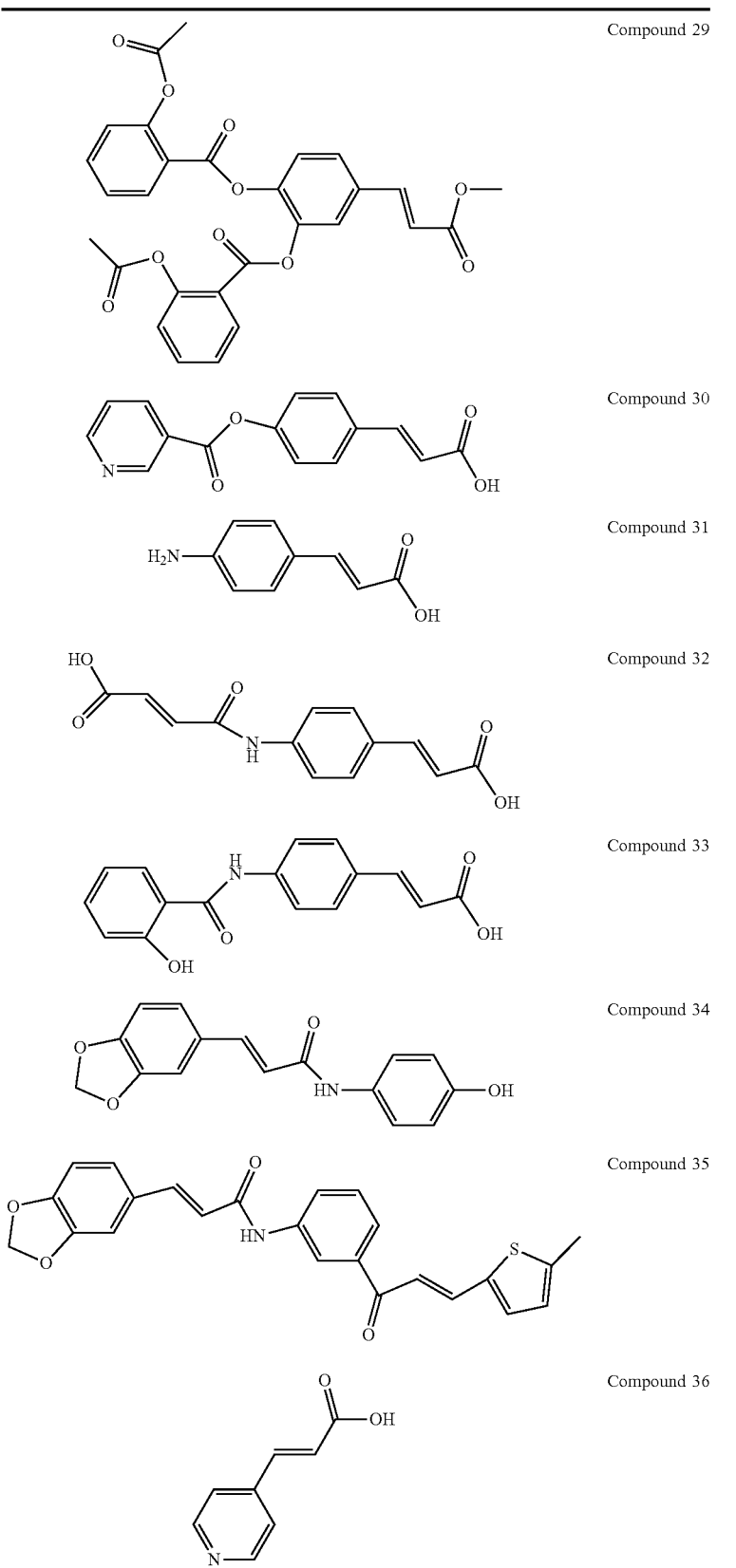
Compound 29
Compound 30
Compound 31
Compound 32
Compound 33
Compound 34
Compound 35
Compound 36

TABLE 2-continued
the structures of Compounds 16 to 46
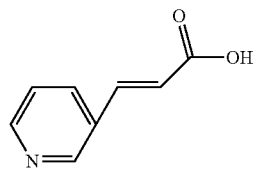 [SMILES: O=C(O)/C=C/c1cccnc1]
Compound 37
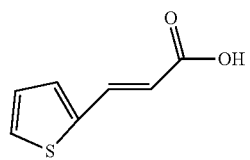
Compound 38
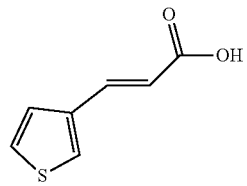
Compound 39
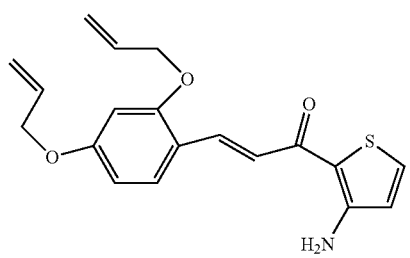 [SMILES: C=CCOc1ccc(/C=C/C(=O)c2sccc2N)c(OCC=C)c1]
Compound 40
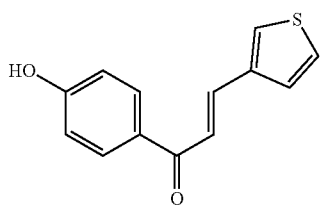 [SMILES: O=C(/C=C/c1ccsc1)c1ccc(O)cc1]
Compound 41
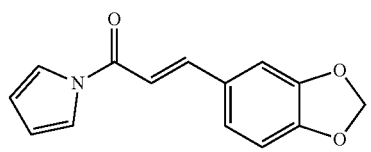 [SMILES: O=C(/C=C/c1ccc2c(c1)OCO2)n1cccc1]
Compound 42
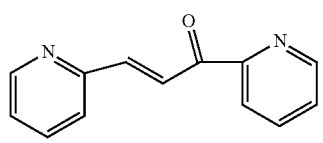 [SMILES: O=C(/C=C/c1ccccn1)c1ccccn1]
Compound 43
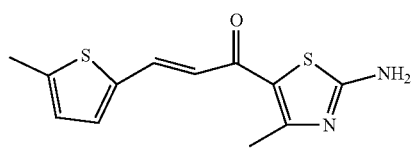 [SMILES: Cc1ccc(/C=C/C(=O)c2sc(N)nc2C)s1]
Compound 44

TABLE 2-continued the structures of Compounds 16 to 46

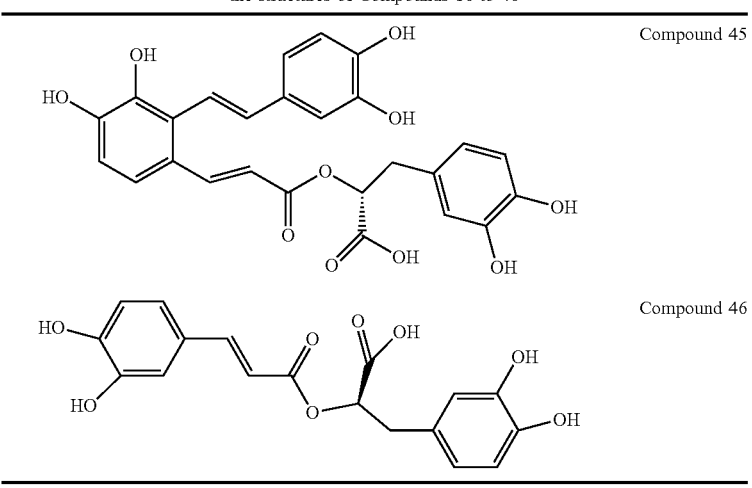

As an active ingredient, the aforementioned Compounds 1 to 46 respectively mix with a pharmaceutically acceptable carrier to from a pharmaceutical composition for promoting myocardial regeneration, a health food for preventing myocardial infarction and a health food for prognosis maintenance of myocardial infarction.

As represented by Formula (II), the aforementioned compounds used for myocardial regeneration may be salt or ester. For example, any one of the compounds represented by Formula (II) reacts with alkali metals or alkaline earth metals to form sodium salt, potassium salt, magnesium salt, calcium salt, ammonium salt, carbonate, nitrate, bicarbonate, hydrochloride, sulfate or silicate. Or, any one of compounds represented by Formula (II) reacts with alcohols to form esters such as methyl ester, ethyl ester, propyl ester, butyl ester, amyl ester, methyl acetate, ethyl acetate, butyl formate, butyl acetate, butyl valerate, butyl propionate, methyl butyrate or ethyl butanoate. The aforementioned "pharmaceutically acceptable carrier" or "acceptable carrier" includes pharmaceutically or food acceptable excipients or additives such as starch, corn starch, gelatin, Arabic gum, food dye, spices, flavoring agent, and preservative substance. Routes of administration include oral administration, skin administration, intraperitoneal administration, intravenous administration, nasal administration or eye administration. The preferred route of administration is oral administration.

According to patient's age, weight, health condition, type of disease, progress of disease, and affected region, the administration dosage of the aforementioned pharmaceutical composition is determined by related medical personnel depending on the common knowledge in the art. The pharmaceutical composition can be administrated alone or accompanied with other drugs. The administration process should be performed by related medical personnel according to the routine method in pharmacy.

The amount of active ingredients in aforementioned health food can be adjusted according to specific groups. Preferably, the amount is suitable for daily intake. The package may be marked with suggested usage, the criteria and conditions of use for specific groups (such as pregnant females or patients with kidney diseases) or other suggestions about taking with other food or drugs, which makes the buyer safe to take without the instructions from doctors, pharmacists or related personnel.

TEST EXAMPLE 1

Evaluation of Activities of Compounds 1 to 46 for Myocardial Regeneration

Myosin is a functionally and structurally important component of myocardium, and is composed of myosin heavy chains. Among them, the α-cardiac myosin heavy chain (α-MHC) is encoded by MYH6 gene that is specifically expressed in myocardial cells during early development of the heart. MYH6 gene is mainly expressed in atrium and plays an important role in contractile function of myocardial cells. The gene also provides recognition clues to the heart for transcriptional regulatory events to participate in myocardial cell lineage induction and maintenance. As α-MHC is an important protein for early development of the heart, the expression level of α-MHC in H9C2 cell line (cardiac myoblast) is a suitable indicator for evaluating the effects of test examples on promoting stem cell differentiation and post-maintenance of myocardial infarction.

1.1: Cell Culture of H9C2 Cell Line

H9C2 cell line is a cardiac myoblast derived from the rats and is purchased from Food Industry Research and Development Institute, Taiwan. The culture medium is 90% (v/v) Dulbecco's modified Eagle's medium with 4 mM L-glutamine (Gibco™, Cat.12800017) adjusted to contain 4.5 g/L glucose and 1.5 g/L sodium bicarbonate (Sigma, Cat.S5761) and 10% (v/v) fetal bovine serum (Gibco™, Cat.10437028). Incubate at 37° C. in a 5% (v/v) $CO_2$ in air atmosphere.

1.2: MTT Assay for Cell Viability Testing

In order to find out the feasible concentration of compounds without cytotoxicity, cells was cultured to 90% confluency and cells were seeded in a 24-well plate at a concentration of $1.5*10^4$ cell/well. After 24 hours, 0.2 to 30 μg/ml of Compounds 1 to 46 and DMSO (Sigma, Cat.D4540) were added for 48 hours treatment (each group was triplicate). After washing with PBS buffer (phosphate buffered saline), 0.5 mg/ml of MTT (Thiazolyl Blue Tetrazolium Bromide; Sigma, Cat.M2128) was added and incubate the 24-well plate at 37° C. for 4 hours. After that, violet crystals were observed by microscope. Then the supernatant was removed and 200 μL DMSO was added to dissolve the crystal. Mix each sample again using a pipette and read absorbance at 570 nm (the values are averages of triplicate). The value of the DMSO group is 100% to represent that the cell viability is 100%. In the following testing, the concentration of compounds with cell viability within 80% to 120% was selected to make sure the growth of myocardial cells was unaffected, as shown in FIG. 1.

1.3: Cell Disruption and Collection

H9C2 cells were cultured at about 90% confluence and were seeded in a 24-well plate at a concentration of $1.5*10^4$ cell/well. After 24 hours, Compounds 1 to 46 and DMSO were added for 48 hours (each group was triplicate) and the concentrations of Compounds 1 to 46 are listed in Table 3. After washing with PBS buffer, 0.05% (w/v) 200 μL/well trypsin was added for 5 minutes. Then cell culture solution was added to terminate trypsin reaction. The cell suspension was centrifuged at 4° C., 1000 rpm for 3 minutes and cells were washed three times with PBS buffer. Afterwards, cells were resuspended in PBS and frozen at −80° C. Thaw cell with gentle mixing. The freeze-thaw cycles were repeated for 3 times to disrupt cells. Finally, the solution was centrifuged at 4° C., 3000 rpm for 15 minutes and the supernatant was collected and then stored at −20° C.

TABLE 3 the concentration of Compounds 1 to 46

| Compound No. | Concentration (μg/ ml) | Compound No. | Concentration (μg/ ml) | Compound No. | Concentration (μg/ ml) |
|---|---|---|---|---|---|
| 1 | 20 | 2 | 20 | 3 | 20 |
| 4 | 20 | 5 | 25 | 6 | 10 |
| 7 | 25 | 8 | 10 | 9 | 20 |
| 10 | 20 | 11 | 1 | 12 | 20 |
| 13 | 15 | 14 | 20 | 15 | 20 |
| 16 | 20 | 17 | 20 | 18 | 1 |
| 19 | 20 | 20 | 20 | 21 | 20 |
| 22 | 10 | 23 | 20 | 24 | 10 |
| 25 | 20 | 26 | 20 | 27 | 10 |
| 28 | 20 | 29 | 20 | 30 | 20 |
| 31 | 10 | 32 | 20 | 33 | 10 |
| 34 | 0.4 | 35 | 20 | 36 | 20 |
| 37 | 10 | 38 | 10 | 39 | 10 |
| 40 | 4 | 41 | 10 | 42 | 0.4 |
| 43 | 20 | 44 | 10 | 45 | 20 |
| 46 | 20 | | | | |

1.4: Determination of the Expression Level of α-MHC

Rat Myosin Heavy Chain 6, Cardiac Muscle Alpha (MYH6) ELISA Kit (MyBioSource, Cat.MBS753946) and ELISA Reader were used to determine the expression level of α-MHC. Then the values of 450 nm absorbance read by ELISA Reader were recorded (the values are averages of triplicate). The value of DMSO group was set as 100% to calculate the relative expression level of α-MHC of groups treated with Compounds 1 to 46.

As shown in FIG. 1, after H9C2 cells were treated with Compounds 1 to 46, the cells still grew normally (cell viability within 80% to 120%) and the expression level of α-MHC of all treated groups increased relative to the group added with DMSO. That is, Compounds 1 to 46 can actually promote the expression level of α-MHC in H9C2 cells, which indicated that Compounds 1 to 46 are able to promote myocardial regeneration and repair.

TEST EXAMPLE 2

Evaluation of the Effects of Compounds 1 to 46 on Myocardial Regeneration of the Zebrafish The injury region (~30%) of the heart of zebrafish caused by frozen wound can repair within 21 days. Accordingly, adult zebrafish is a suitable animal model for studying heart damage. After the heart of the zebrafish is damaged, the regeneration process include three stages: the first is proliferation of myocardial cells; the second is regeneration of pericardial cells; and the last is regeneration of endothelial cells of blood vessels.

In order to evaluate the effects of compounds for myocardial regeneration and repair, transgenic zebrafish (Tg-flil-eGFP) was adopted and anesthetized to performed heart frozen wound. Accordingly, the endothelial cells of blood vessels of the transgenic zebrafish can express the green fluorescent protein. After the heart of the zebrafish was damaged by frozen wounding, the injury cells cannot express the green fluorescent protein, which can evaluate the injury region of the heart.

2.1: Performance of Heart Injury on Adult Zebrafish

A cryoprobe 6 mm long and 0.8 mm wide was used to perform heart frozen wounding on zebrafish. To perform the heart injury, an anesthetized adult zebrafish was placed in the slit of a sponge with its ventral side up. The skin and muscle between two pectoral fins were cut open and then the silvery hypodermis beneath was gently opened by tweezer to access the heart. After that, the cryoprobe was gently inserted into the chest to contact the heart for cryoinjury.

In order to evaluate the regeneration and repair of the heart of the zebrafish, heart collecting has to be performed. When conducting heart collection, the branchial arch of the chest was cut open to reach the pericardial chamber, and to show the arterial ball and the ventricular. Then arterial forceps were used to remove the arterial ball and the heart was excided to finish the heart harvesting process.

In the present invention, any experimental process related to cryoinjury or heart collecting is same as the aforementioned procedures.

2.2: Evaluation the Effects of Compounds 1 to 46 on Myocardial Regeneration of Zebrafish After the cryoinjury was performed on the transgenic zebrafish, the transgenic zebrafish was fed with 12.5 μg/g test example daily for 7 days. In day 8, the zebrafish was sacrificed to perform heart collecting for calculating the injury region of the heart and further evaluating the effects of promoting myocardial regeneration and repair on the zebrafish.

Because the endothelial cells of blood vessels of the transgenic zebrafish can express the green fluorescent protein, the fluorescent areas can represent the region without damage. That is, the areas without fluorescence were the injury region and its proportion to the heart can be calculated to obtain the percentage of the cryoinjury area.

Figure 2:
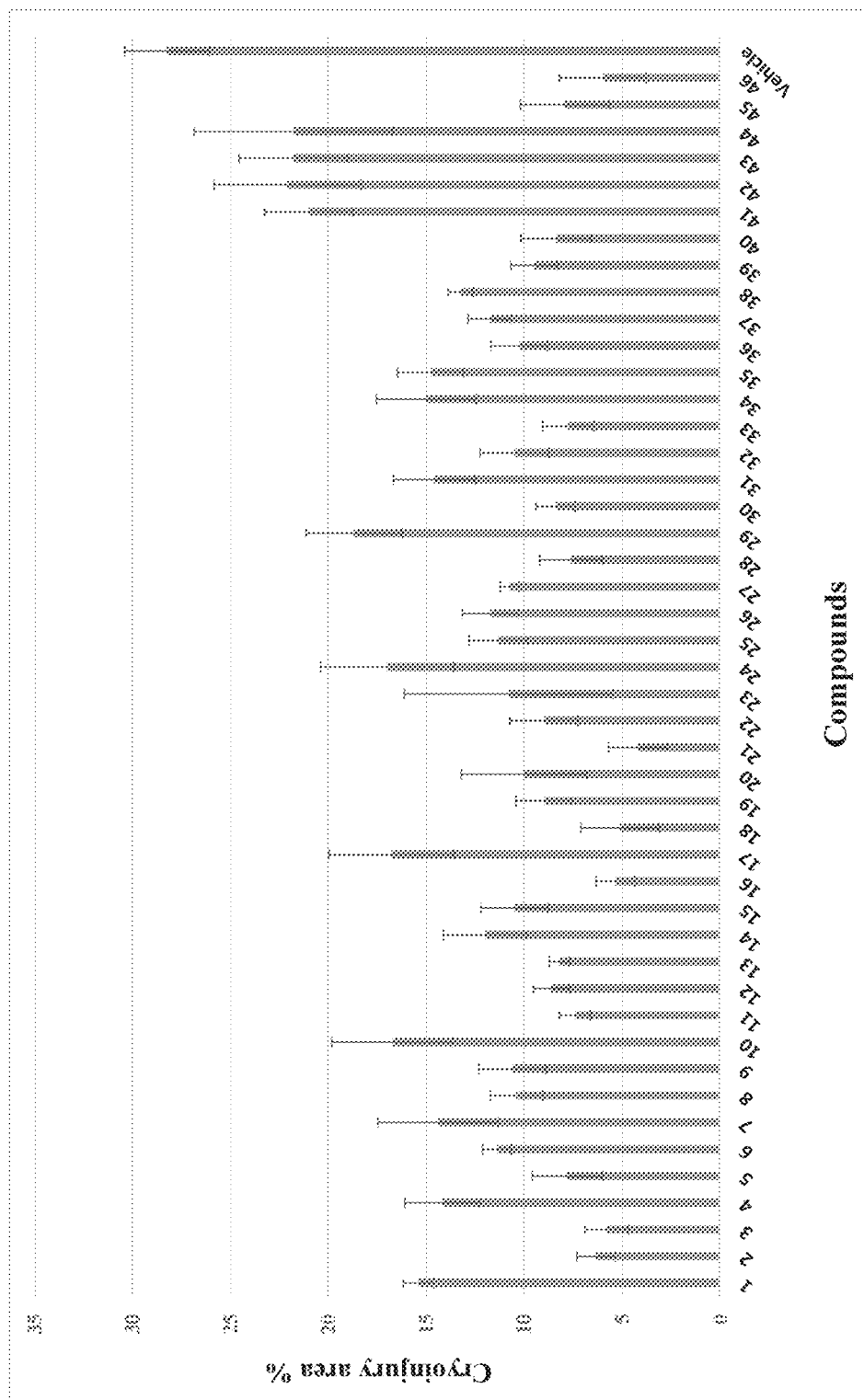
FIG. 2 shows the percentage of the cryoinjury areas of the heart of zebrafish after fed with compositions respectively containing Compounds 1 to 46.

The group fed with test example only containing solvent was denoted as vehicle. In order to confirm the percentage of the injury area of the vehicle, the heart injury zebrafish was fed with test example only containing solvent for 7 days and the percentage of the cryoinjury area was 27%. Then the heart injury zebrafishes were fed with test examples respectively containing Compounds 1 to 46 for 7 days and the percentage of the cryoinjury area of every group was calculated and shown in FIG. 2. According to the results shown in FIG. 2, the percentage of the cryoinjury area of all groups fed with test examples respectively containing Compounds 1 to 46 for 7 days obviously decreased compared to the result in vehicle. That is, Compounds 1 to 46 can actually promote myocardial regeneration and repair of zebrafish.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A compound represented by Formula (I) below:

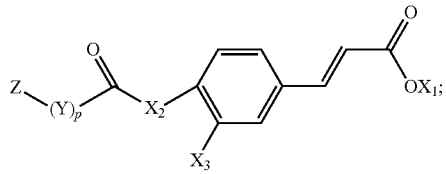

Formula (I)

where $X_1$ is a hydrogen atom or an unsubstituted alkyl group having 1 to 6 carbon atoms;

$X_2$ is an oxygen atom or an amino group;

$X_3$ is a hydrogen atom, a hydroxyl group, or *—$X_2$—(CO)—$(Y)_p$—Z group;

Y is an alkylene group having 1 to 6 carbon atoms, an alkenylene group having 2 to 12 carbon atoms, an arylenealkylene group having 7 to 18 carbon atoms, or an arylene group having 6 to 18 carbon atoms;

Z is *—COCH$_3$, *—COOH, *—COOCH$_3$, *—OCOCH$_3$, *—NHCOOC(CH$_3$)$_3$, *—F, *—Cl, *—Br, or *—I; and p is 0 or 1, wherein, when $X_1$ is a hydrogen atom, $X_3$ is a hydrogen atom, and Y is an arylenealkylene group having 7 to 18 carbon atoms, Z is *—COOH, *—COOCH$_3$, *—OCOCH$_3$ or *—NHCOOC(CH$_3$)$_3$;

wherein, when $X_1$ is a hydrogen atom, $X_3$ is a hydrogen atom, and Y is an arylene group having 6 to 18 carbon atoms, Z is *—COCH$_3$, *—COOH, *—OCOCH$_3$, or *—NHCOOC(CH$_3$)$_3$; or wherein, when $X_1$ is a hydrogen atom, $X_3$ is a hydrogen atom, and Y is an alkylene group having 1 to 6 carbon atoms or an alkenylene group having 2 to 12 carbon atoms, Z is *—COCH$_3$, *—COOH, *—COOCH$_3$, *—OCOCH$_3$, *—NHCOOC(CH$_3$)$_3$, *—F, *—Cl, *—Br, or *—I, wherein, when $X_1$ is an unsubstituted alkyl group having 1 to 6 carbon atoms and Y is an arylene group having 6 to 18 carbon atoms, Z is *—COCH$_3$, *—COOH, *—COOCH$_3$, *—NHCOOC(CH$_3$)$_3$, *—F, *—Cl, *—Br, or *—I, and wherein, when $X_1$ is an unsubstituted alkyl group having 1 to 6 carbon atoms and Y is an alkylene group having 1 to 6 carbon atoms, an alkenylene group having 2 to 12 carbon atoms or an arylenealkylene group having 7 to 18 carbon atoms, Z is *—COCH$_3$, *—COOH, *—COOCH$_3$, *—OCOCH$_3$, *—NHCOOC(CH$_3$)$_3$, *—F, *—Cl, *—Br, or *—I.

2. The compound as claimed in claim 1, wherein Z is *—COOH, *—COOCH$_3$, *—OCOCH$_3$, *—NHCOOC(CH$_3$)$_3$, or *—Cl.

3. The compound as claimed in claim 1, wherein $X_2$ is

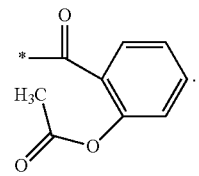

or *—NX$_4$—*, and $X_4$ is

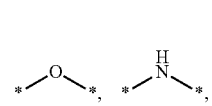

4. The compound as claimed in claim 1, wherein Y is a butylene group, a vinylene group, a cresylene group, or a phenylene group.

5. The compound as claimed in claim 1, wherein the compound represented by Formula (I) is selected from the group consisting of:

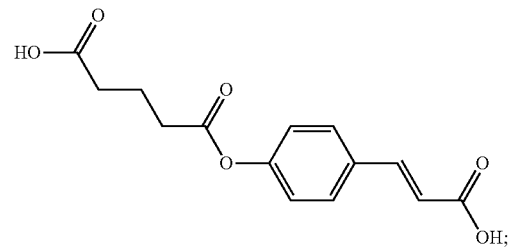

Compound 1

-continued
Compound 2
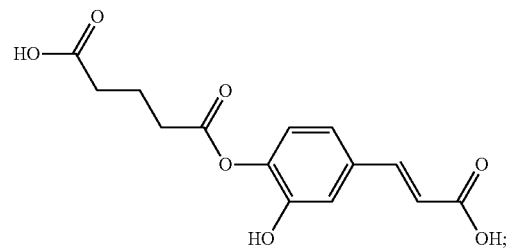
Compound 3
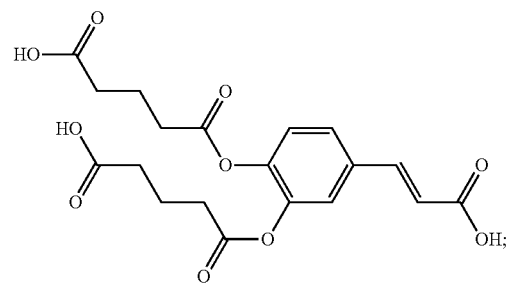
Compound 4
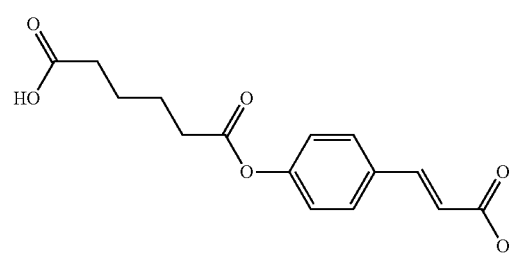
Compound 5
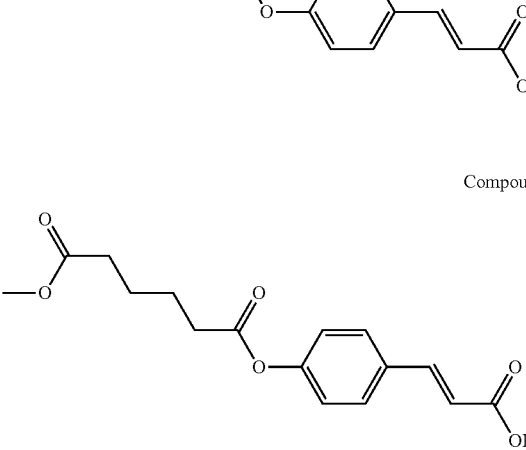
Compound 6
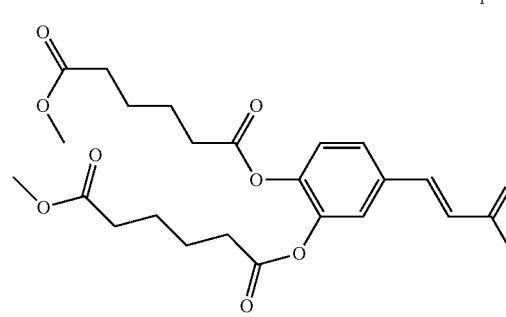
-continued
Compound 7
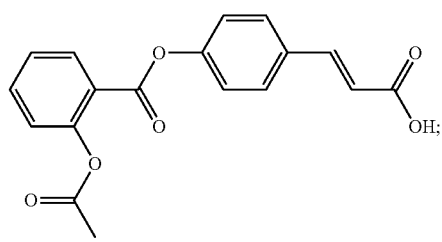
Compound 8
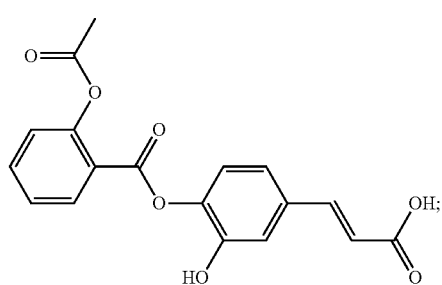
Compound 9
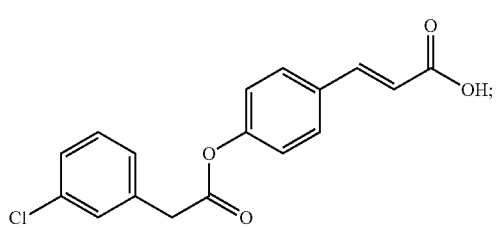
Compound 10
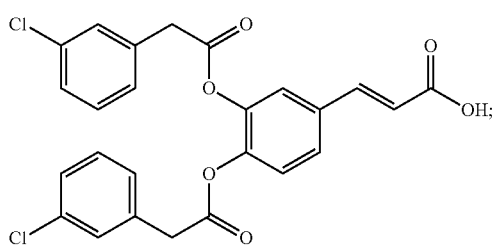
Compound 11
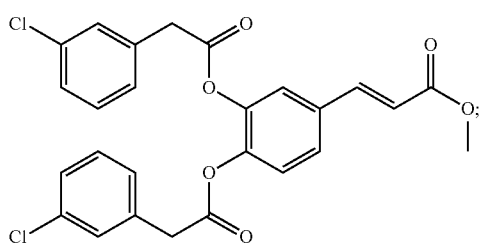

-continued

Compound 12

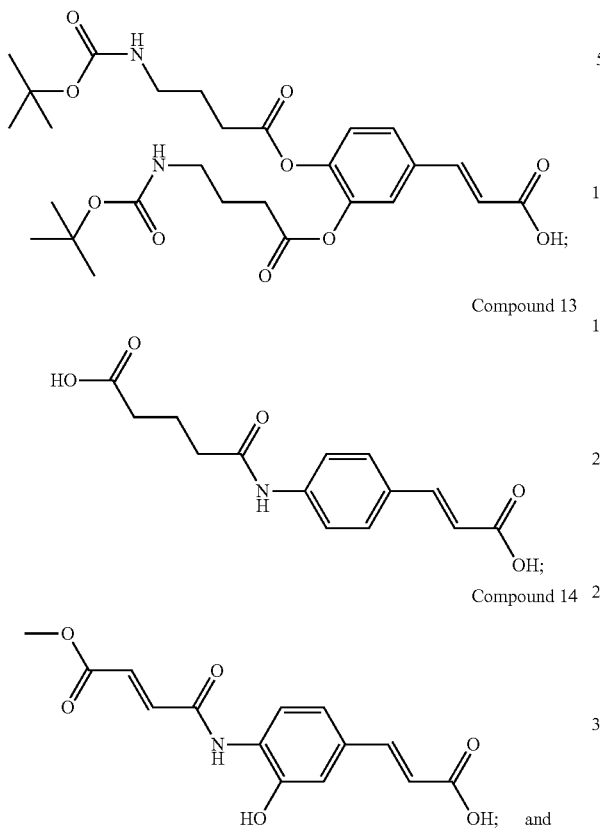

Compound 13

Compound 14

Compound 15

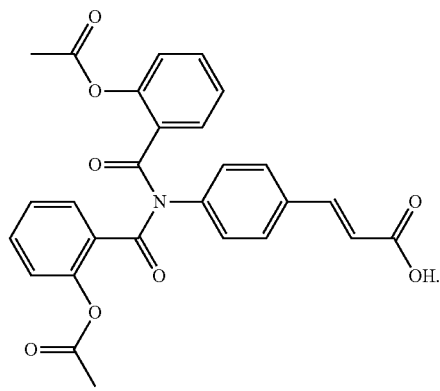

6. A preparation method of the compound as claimed in claim 1, comprising the steps of:
   reacting a reactant A with a reactant B at a temperature of 0° C. to 25° C.,
   wherein the reactant A is para-coumaric acid, caffeic acid, methyl caffeate, or 4-aminocinnamic acid; and the reactant B is acetylsalicylic acid, 3-chlorophenylacetic acid, n-tert-butoxycarbonyl-γ-aminobutyric acid, glutaric anhydride, adipic anhydride, methyl adipoyl chloride, or fumaric acid monomethyl ester.

7. The preparation method as claimed in claim 6, wherein the reaction of the reactant A and the reactant B is performed at 0° C. to 25° C. under alkaline conditions.

8. A pharmaceutical composition for promoting myocardial regeneration comprising the compound as claimed in claim 1 and a pharmaceutically acceptable carrier.

\* \* \* \* \*